(12) United States Patent
Laham et al.

(10) Patent No.: US 8,038,595 B2
(45) Date of Patent: Oct. 18, 2011

(54) DEVICES AND METHODS FOR TISSUE TRANSPLANT AND REGENERATION

(75) Inventors: Roger J. Laham, Brookline, MA (US); Joanna J. Wykrzykowska, Boston, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 1272 days.

(21) Appl. No.: 11/339,320

(22) Filed: Jan. 25, 2006

(65) Prior Publication Data

US 2007/0238177 A1  Oct. 11, 2007

(51) Int. Cl.
*A61F 2/08* (2006.01)
(52) U.S. Cl. .......................... 600/37; 600/567
(58) Field of Classification Search .............. 600/37; 623/918; 604/506, 511
See application file for complete search history.

(56) References Cited

U.S. PATENT DOCUMENTS

| | | | |
|---|---|---|---|
| 3,342,175 A | 9/1967 | Bulloch | |
| 5,006,122 A | 4/1991 | Wyatt et al. | |
| 5,810,746 A | 9/1998 | Goldstein et al. | |
| 5,871,495 A | 2/1999 | Mueller | |
| 5,888,720 A | 3/1999 | Mitrani | |
| 5,976,164 A | 11/1999 | Bencini et al. | 606/170 |
| 5,980,885 A * | 11/1999 | Weiss et al. | 424/93.21 |
| 6,099,832 A | 8/2000 | Mickle et al. | 424/93.21 |
| 6,102,926 A | 8/2000 | Tartaglia et al. | |
| 6,110,459 A | 8/2000 | Mickle et al. | 424/93.21 |
| 6,432,712 B1 | 8/2002 | Wolfinbarger, Jr. | 435/395 |
| 6,485,436 B1 | 11/2002 | Truckai et al. | |
| 6,638,233 B2 | 10/2003 | Corvi et al. | |
| 6,659,995 B1 | 12/2003 | Taheri | |
| 6,758,848 B2 | 7/2004 | Burbank et al. | |
| 6,893,421 B1 | 5/2005 | Larson et al. | |
| 6,918,890 B2 | 7/2005 | Schmidt | |
| 7,067,121 B2 | 6/2006 | Mickle et al. | 424/93.21 |
| 7,097,833 B2 | 8/2006 | Freyman | 424/93.7 |
| 7,131,994 B2 * | 11/2006 | Mills et al. | 623/14.13 |
| 7,211,067 B2 | 5/2007 | Hawk et al | |
| 7,297,540 B2 | 11/2007 | Mitrani | |
| 7,309,328 B2 | 12/2007 | Kaplan et al. | |

(Continued)

FOREIGN PATENT DOCUMENTS

WO  WO 98/22026  5/1998

(Continued)

OTHER PUBLICATIONS

Borenstein et al., "Noncultured, Autologous, Skeletal Muscle Cells Can Successfully Engraft into Ovine Myocardium", www.circulationaha.org, p. 3088-3092, Jun. 2003.

*Primary Examiner* — Charles A Marmor, II
*Assistant Examiner* — Carrie R Dorna
(74) *Attorney, Agent, or Firm* — Weingarten, Schurgin, Gagnebin & Lebovici LLP

(57) ABSTRACT

Devices and methods for transplanting tissue for the purpose of regeneration, for treating a patient having injured myocardial tissue, and/or for improving cardiac function through cell regrowth. More specifically, the devices and methods obviate the need for cellular alteration. The devices comprise a hollow tube with a sharp distal end, a stylet that is disposed and movable within the hollow tube, and a stopping device that constrains movement of the stylet. The methods comprise removing intact tissue from a first region of a mammalian organ and implanting the tissue in a second region of the same organ.

40 Claims, 20 Drawing Sheets

U.S. PATENT DOCUMENTS

| | | |
|---|---|---|
| 2002/0183740 A1 | 12/2002 | Edwards et al. |
| 2003/0086914 A1 | 5/2003 | Mitrani |
| 2004/0097973 A1 | 5/2004 | Loshakove et al. |
| 2005/0124975 A1 | 6/2005 | Law |
| 2005/0288618 A1 | 12/2005 | Jenson et al. |
| 2006/0041243 A1* | 2/2006 | Nayak et al. ............... 604/506 |
| 2006/0189891 A1 | 8/2006 | Waxman et al. |
| 2006/0263338 A1 | 11/2006 | Jacoby et al. ............... 424/93.7 |
| 2006/0276685 A1 | 12/2006 | Dinsmore .................... 600/37 |
| 2007/0059288 A1 | 3/2007 | Dinsmore et al. ........... 424/93.2 |

FOREIGN PATENT DOCUMENTS

| | | |
|---|---|---|
| WO | WO 98/54301 | 12/1998 |
| WO | WO 01/00859 | 1/2001 |
| WO | WO 02/28470 | 4/2002 |
| WO | WO 03/060062 | 7/2003 |
| WO | WO 03/061455 | 7/2003 |
| WO | WO 2004/009132 | 1/2004 |
| WO | WO 2005/112817 | 12/2005 |
| WO | WO 2006/005342 | 1/2006 |

* cited by examiner

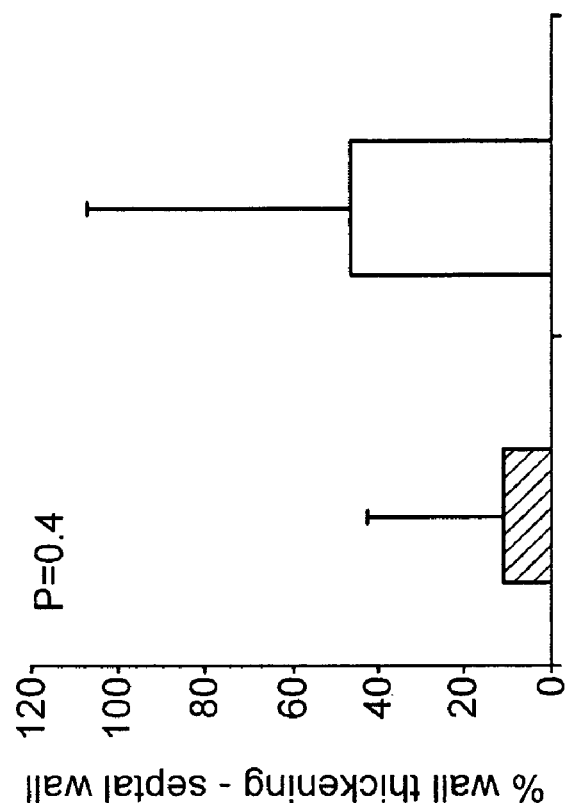
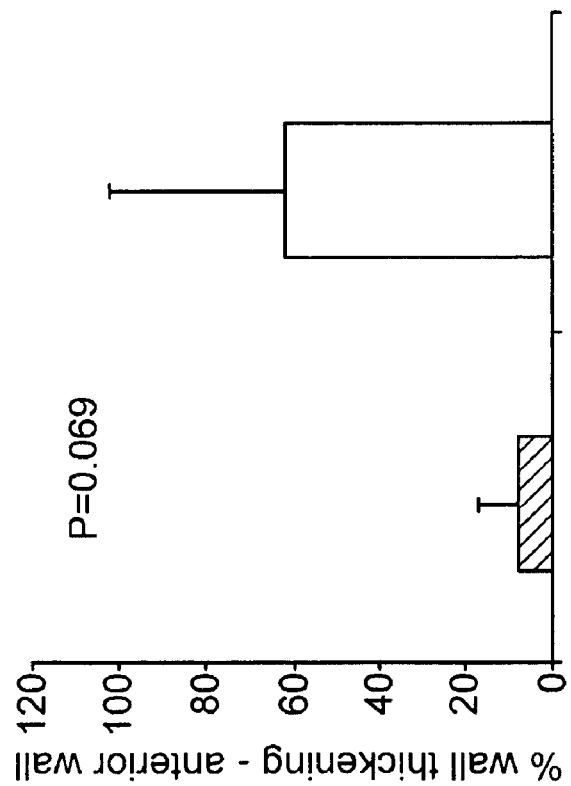
FIG. 6A
FIG. 6B

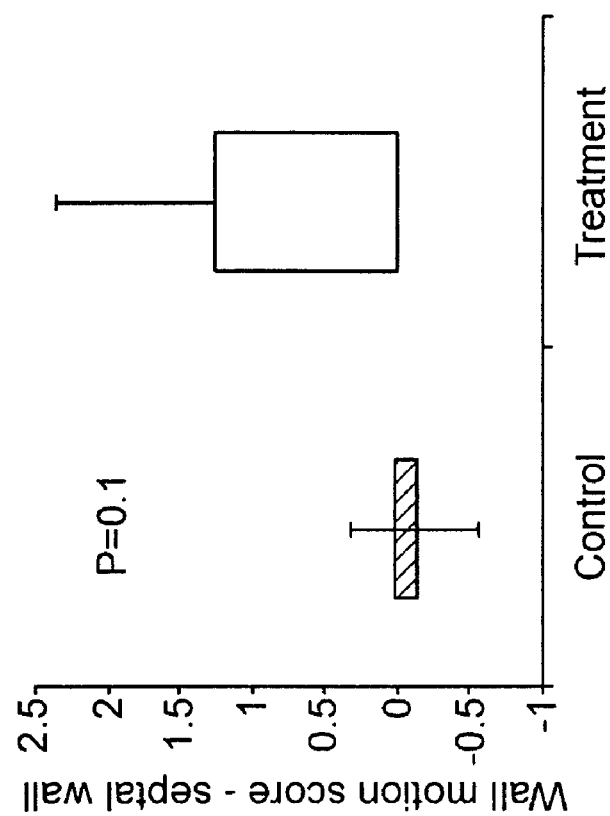
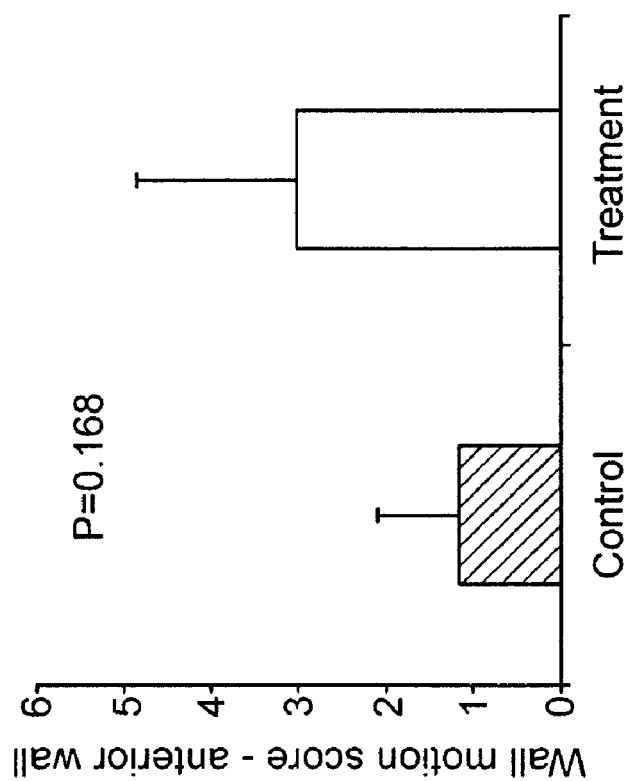

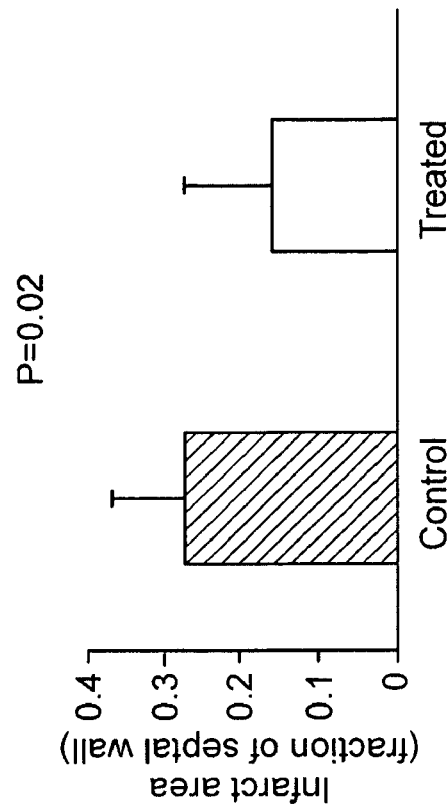
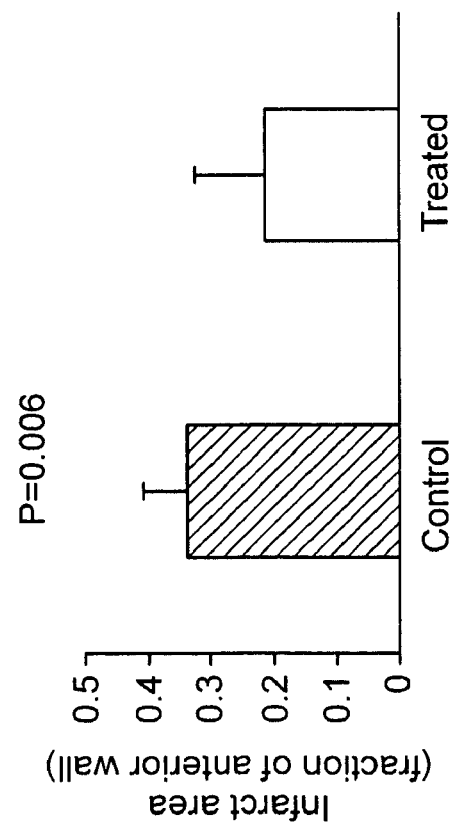
FIG. 12B
FIG. 12A

DEVICES AND METHODS FOR TISSUE TRANSPLANT AND REGENERATION

BACKGROUND OF THE INVENTION

Myocardial infarction and ischemic heart disease in adult humans can result in dysfunction and irreversible cardiomyocyte loss, which damage and weaken the heart muscle. Cardiomyocyte loss and heart damage, if untreated, can lead to congestive heart failure, a leading cause of mortality, within a few years of the myocardial infarction or ischemia.

Myocardial functionality, especially among aging adult humans, typically, cannot be restored using a body's inherent healing mechanisms. Myocardial regeneration of cardiomyocytes in adult humans is also very limited. Furthermore, myocardial transplantation is restricted by a shortage of organ donors. Accordingly, means and methods of myogenesis and/or myocardial regeneration to supplement the adult human body's natural healing capability have become the subject of intensive research and investigation.

Cell transplantation, e.g., cellular cardiomyoplasty, is a method of replacing cardiomyocytes lost due to myocardial infarction or ischemia. Succinctly, autologous cells from other parts of the body or exogenous cells can be transplanted or engrafted in the myocardium. The transplanted or engrafted cells differentiate and, for reasons that are not fully known at this time, provide functional improvement of the myocardium.

A myriad of different cell types have been used for such cellular, or cell-based, therapies. For example, cell-based therapies have included, without limitation, adult cultured cardiac and skeletal muscle myocytes or myoblasts, progenitor cells from autologous bone marrow and/or peripheral blood, cultured mesenchymal and/or embryonic stem cells.

To enhance cell-growth, extracted cells regardless of their source of origin can be artificially cultured. Cell culturing involves harvesting autologous muscle cells or tissue, blood cells, stem cells, culturing the cells or tissue in vitro or in vivo to provide a higher cell density and introducing the cultured cells in the damaged portion of the myocardium. Historic problems with cell culturing include the expense, the potentially hazardous nature of the harvesting process, the time needed to culture the cells, and the equipment needed to harvest and implant the cells.

Methods for improving myocardial functionality include retrieving myocyte micro-granules from a donor area placing the myocyte micro-granules in a fluid container and implanting the myocyte micro-granule fluid.

There is a continuing need for improvement in systems and methods for cellular regeneration of tissue.

SUMMARY OF THE INVENTION

The present invention discloses devices and methods for transplanting tissue from a first region of a mammalian internal organ, e.g., the myocardium, brain, liver, kidney, or bladder to a second region of the mammalian internal organ. Preferably, the method comprises removing a tissue sample from the first region of the mammalian organ and implanting the tissue sample in the second region of the mammalian organ to increase cellular growth in the second region. In this embodiment, it is preferable that the removal and implantation steps do not include an intermediate step of cellular alteration. By preserving the tissue architecture during tissue removal and implantation, the process can increase the number of resident stem cells.

In one aspect of the embodied method, when the mammalian organ is the myocardium, the method further includes removing the tissue sample from intact myocardial tissue and, more specifically, from the ventricle septum of the heart. The volume of tissue removed for cardiomyoplasty is selected so as to minimize damage to healthy tissue that will quickly heal, and at the same time provide a population of cardiac stem cells that preserves or improves cardiac function in the damaged region.

In another aspect of the embodied method, the myocardial biopsy tissue is implanted into ischemic myocardial tissue and/or a myocardial infarction (MI) region. It is preferable to perform the procedure as soon as possible after the damage to the tissue has occurred. However, the procedure is advantageous even if performed well after the initial injury.

In another embodiment, the present invention provides a method of treating a mammalian subject having injured myocardial tissue. Preferably, the method comprises removing a tissue sample from a first region of mammalian myocardial tissue and implanting the tissue sample in a second region of injured mammalian myocardial tissue to enhance cellular growth. Depending upon the size of the injured region, the surgeon can optionally perform additional tissue removal and implants at different locations to increase the rate of cellular regeneration. Thus, 2-10 or more implants can be performed for a given patient.

In still another embodiment, the present invention provides a method of improving cardiac function in a mammalian subject having an injured myocardium. Preferably, the method comprises removing a tissue sample from a first region of a mammalian myocardium and implanting the tissue sample in a second region of the mammalian myocardium to improve cardiac function by cellular regrowth. This can include, for example, improved ejection fraction and contractility of the heart.

A preferred embodiment of the invention provides a device for repairing an injured myocardium by cellular regrowth. In a preferred embodiment, the device comprises a tube having a sharp distal end for insertion into myocardial tissue, a stylet movable within the tube that moves a tissue sample within the tube and a stopping device positioned within the tube that constrains movement of the stylet. The embodied device is further suitable for retrieving a tissue sample from a donor area for implantation in a portion of a myocardium without cellular alteration of the sample and/or for transplanting tissue from a first region of a mammalian organ to a second region of the mammalian organ. The device can be employed during an open heart or minimally invasive procedure to remove and implant myocardial tissue or can be used with a percutaneous catheter system to remove and implant tissue. The device removes a volume of tissue in a range of 2 to 10 mm$^3$. The sample is preferably small enough that blood will readily move through the sample at a rate that will avoid necrosis.

The thickness of the septum determines the length of the biopsy taken which in humans ranges between 10 and 13 mm. Thus the technique takes advantage of the septal anatomy to make the tissue volume and dimensions uniform. This also allows for the biopsy device to act as a cutting device without the need for tissue shearing and damage. The hypotube is about 200-800 um in inner diameter. This determines the thickness of the sample which falls within the range of diffusion of blood and therefore does not require the implants to be transplanted with their own blood supply.

In another preferred embodiment of the invention, all or a portion of the removed tissue undergoes a further diagnostic or therapeutic treatment. The catheter delivery system and the myotissue implant process can also include septal biopsies that are subjected to digestion with urea which empties the extracellular matrix scaffold of its cellular elements. The matrix scaffold thus engineered can be subsequently repopulated with other cellular elements. Different cell types within the scaffold can thus be implanted within the myocardium and their potential to regenerate the myocardium and promote angiogenesis can be assessed. These cell types can include endothelial cell progenitors, smooth muscle cell progenitors or cardiomyocyte progenitors. In addition cord blood derived stem cells can also be used with this method.

Thus, the present invention utilizes a tissue scaffold or extracellular supporting tissue structure that supports a sufficient population of cells to enhance cellular regeneration of the organ. By using the selected volume of tissue, the extracellular in lieu of the sample, can be used to further improve the regeneration properties of the implant.

In addition, the scaffold with or without the cellular elements can be infused with angiogenic proteins (VEGF, FGF-2, HIF-1 and PR39) and other growth factors and thereby form a platform into which cardiac resident stem cells can migrate and in which they can find a trophic environment to grow and differentiate into mature cardiomyocytes.

Genetically engineered cells can also be implanted using this scaffold vehicle and the catheter system described herein. For instance VEGF, PI3 Kinase or Akt transfected cardiomyocytes or endothelial progenitors can be implanted. These growth factors and signaling proteins have been shown to enhance cell survival and decrease apoptosis.

This method is useful for evaluating and using individual angiogenic factors and myogenic cells and their respective regenerative properties. The scaffold allows for more sustained release of these factors rather than short-term increase in levels seen with currently available direct intramyocardial injection methods of naked cDNA.

A preferred embodiment of the invention employs a method of removing a sample in which that portion of the organ being removed has a thickness that is selected to provide a sample of a desired length. For example, in an embodiment in which it is desirable to implant a sample having a length of 5 mm, a portion of the septal wall having a thickness of 5 mm is selected for removal. This avoids the difficulty of having to cut or tear off the end of the sample from the surrounding tissue. Another embodiment involves sampling a portion of the brain in which the sampling device is inserted through the region to be sampled such that the distal end extends into a $3^{rd}$ ventricle or other cavity.

Regeneration of brain tissue can be performed in an analogous fashion to the cardiac muscle, as the brain also has limited regenerative capability. Patients affected with stroke often suffer irreversible neuron loss in the territory of one artery such as middle cerebral artery. The administration of thrombolytics to recanalyze the cerebral artery is even more time sensitive than recanalization of coronary artery during myocardial infarction as neurons are more sensitive to hypoxia. If neuronal resident stem cells are present within the brain tissue, a similar method can be applied whereby brain tissue from frontal lobes or other regions of the brain with redundant function can be implanted into the critical executive function areas of the brain that were damaged by infarction. Computer-assisted endoscopy for neurosurgical procedures can be used to obtain biopsies of the frontal lobe. The site of the biopsy can be predetermined with stereotactic mapping prior to the biopsy procedure to ensure that vital areas are not damaged. Subsequently the biopsy/implantation catheter can be inserted with the aid of the endoscope and with CT guidance to the area of brain infarction.

Another preferred embodiment of the invention includes methods for measuring or monitoring the performance of the organ after implantation such as measuring perfusion, infarct volume, contractility, wall motion and ejection fraction by magnetic resonance imaging (MRI).

BRIEF DESCRIPTION OF THE DRAWINGS

The invention will be more fully understood by referring to the Detailed Description of the Invention in conjunction with the Drawings, of which:

FIGS. 6A and 6B illustrate wall thickening in the anterior and septal wall, respectively, as measured by MRI.

FIGS. 7A and 7b shows anterior and septal wall motion as measured by MRI.

FIGS. 12A and 12B show the improvement in the infarcted region size in treated animals in the interior and septal walls, respectively;

DETAILED DESCRIPTION OF THE INVENTION

The present invention relates to devices and methods for removing a tissue sample from a mammalian organ and implanting the tissue sample into another region of the organ. The devices and methods can be used for cardiomyoplasty, i.e., for use with a human myocardium, and can also be used with other mammalian organs, e.g., the liver, the bladder, the kidneys and the brain. The invention is of particular significance with respect tot he heart and brain in which organ or tissue transplant is not available or difficult, or where current methods of treatment are not adequate.

As previously mentioned, a variety of cells have been proposed for cellular cardiomyoplasty, e.g., adult cultured cardiac and skeletal myocytes, mesenchymal and/or embryonic stem cells, progenitors cells from autologous bone marrow and/or peripheral blood.

However, typically, cardiac stem cells implanted in an infarct zone may not form fully mature cardiomyocytes. More specifically, cardiomyocytes remained small and did not fully differentiate, producing small "islands" of cardiomyocytes.

In a first embodiment, the present invention provides a method of transplanting tissue or cells from a first region of a mammalian organ to a second region of the mammalian organ. More particularly, the method transplants intact myocardial biopsy tissue removed from the ventricle septum into a myocardial infarct region of tissue. Preferably, the method comprises removing a cell or tissue sample, i.e., intact myocardial biopsy tissue, from a first region of the mammalian organ, e.g., the myocardial or ventricle septum, and implanting the cell or tissue sample in a second region of the mammalian organ, i.e., the myocardial infarct scar or ischemic myocardial tissue. More preferably, the cell or tissue sample is implanted without an intermediate step involving cellular alteration.

Figure 1:
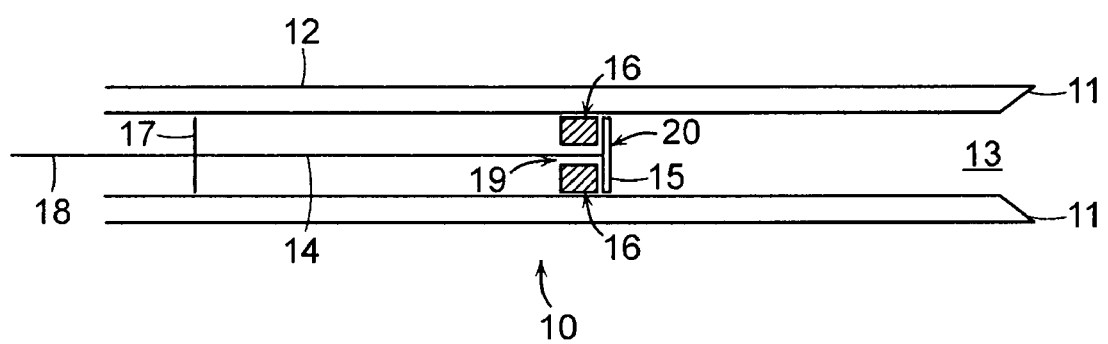
FIG. 1 provides an illustrative embodiment of a retrieval and implantation device in accordance with the present invention.

In one aspect of the present invention, a single device, i.e., a combined bioptome and implantation device, is used both to remove and to implant the cells or tissues. Referring to FIG. 1, there is shown an illustrative embodiment of device 10 in accordance with the invention. Preferably, the device 10 comprises a hollow tube or catheter 12, an internal stylet 20, and a stopping device 16.

Preferably, the hollow tube 12 is made of stainless steel or Nitinol and includes razor-sharp cutting edges 11 around the periphery of the distal end or tip 13 of the tube 12. The hollow tube 12 can be structured and arranged as a rigid, stand alone surgical instrument or, alternatively, it can be structured and arranged as a rigid tip disposed at the distal end of a percutenous flexible shaft.

Effective sampling and implanting can be practiced with a tube 12 having an internal diameter between about 200 and about 800 micrometers (μm). However, larger or smaller diameter tubes 12 can, of course, be used without violating the scope and spirit of this disclosure. Furthermore, a rigid surgical device 10 can be about 30 centimeters (cm) in length whereas the rigid tip disposed on a flexible shaft can be about 2 cm in length.

The stopping device or element 16, e.g., a rubber or plastic O-ring, and the like that includes a central opening 19, is disposed at a discrete distance, e.g., between about 0.5 cm and 2.0 cm, from the distal tip 13 of the tube 12. Preferably, the stopping device 16 is fixedly attached, e.g., adhesively, to or provides a tight interference fit with the inner periphery of the hollow tube 12. The stopping device 16 can arrest or limit movement of the stylet 20 during both an intake stroke and an implant stroke and controls the size or volume of the myocardial biopsy tissue taken and implanted.

The stylet 20 is positioned within the hollow portion of the tube 12 and is structured and arranged to be movable in an axial direction within the tube 12. Preferably, the stylet 20 includes a front or distal portion 15, a rear or proximal portion 17, a stroke shaft 14, and a shaft 18. More preferably, the stylet 20 is structured and arranged so that the stopping device 16 is disposed between the distal 15 and the proximal portions 17 so that the stroke shaft 14 is movable within the central opening 19.

Referring to FIGS. 2A to 2D, the step of removing intact myocardial biopsy tissue from the myocardial or ventricle septum using a rigid device 10, e.g., for an open chest procedure, will be described. Typically, for an open chest procedure, the device 10 is about 30 cm in length.

Figure 2A:
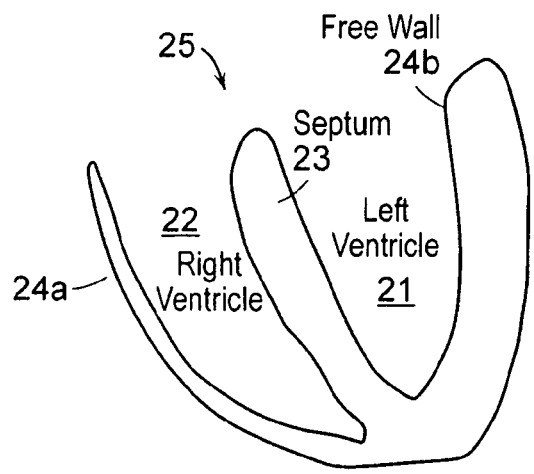
FIG. 2A provides a diagram of a human myocardium.
Figure 2B:
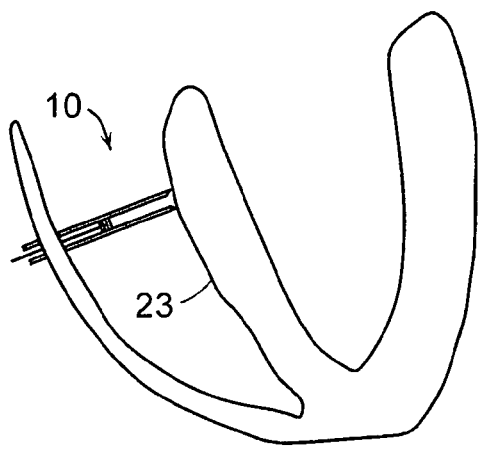
FIGS. 2B and 2C provide illustrations of a method of retrieving intact myocardial tissue using a rigid device in accordance with the present invention.
Figure 2C:
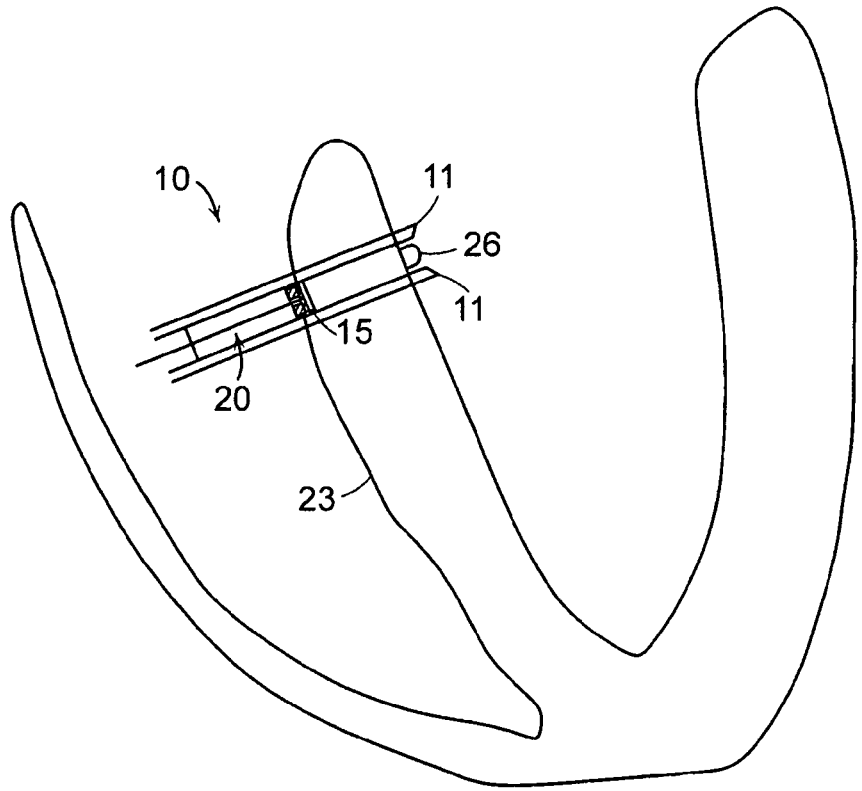

FIG. 2A provides a diagram of a human myocardium 25 that includes a left ventricle 21, a right ventricle 22, and a ventricle septum 23. As shown in FIGS. 2B and 2C, the device 10 is inserted through the wall 24a of the right ventricle 22, e.g., using a 3 Fr sheath or other techniques that are well known under fluoroscopic visualization in the art. The razor-sharp edges 11 of the hollow tube 12, e.g., a cutting cannula, are pressed into the septum 23. As the razor-sharp edges 11 advance further into the septum 23, the myocardial biopsy tissue 26 enters the distal end 13 of the hollow tube 12, displacing the stylet 20 by pushing against the front portion 15.

Once the front portion 15 displaces a discrete distance, e.g., about one (1) cm, from the distal end 13 of the hollow tube 12, the device 10, including the myocardial biopsy tissue 26, can be removed.

Figure 2D:
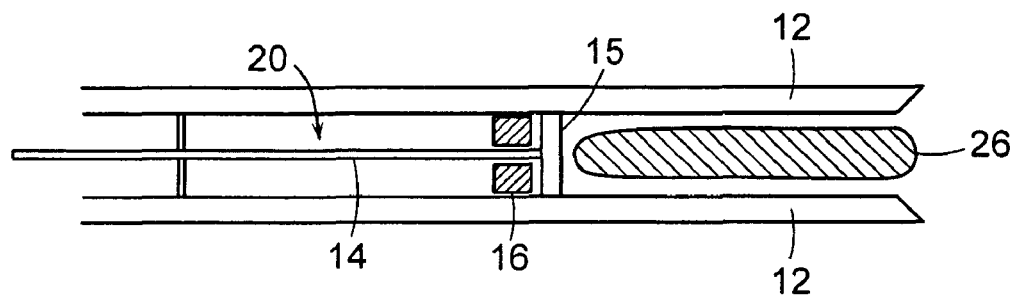
FIG. 2D provides an illustrative embodiment of a retrieval and implantation device during an intake stroke.

FIG. 2D provides an illustrative diagram of the sampling stroke of the device 10. Particularly, the stylet 20 has been pushed progressively backwards by the myocardial biopsy tissue 26 as it entered the hollow tube 12. Once the stopping device 16 and front portion 15 make contact, any further movement of the stylet 20 is arrested and the desired volume of myocardial biopsy tissue 26 is contained in the device 10.

Referring to FIGS. 3A to 3F, the step of implanting the myocardial biopsy tissue 26 in a second region of the mammalian organ using a rigid device 10 will be described. Preferably, the device 10 delivers myocardial biopsy tissue 26 to the treatment area 27 epicardially. More preferably, as previously mentioned, the embodied method obviates an intermediate, e.g., a cell culturing, step. Accordingly, myocardial biopsy tissue 26 retrieved in the first step can be implanted without cell culturing.

Figure 3A:
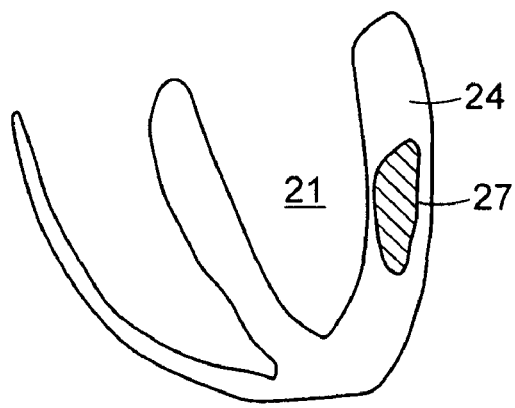
FIG. 3A provides a diagram of a human myocardium with a treatment area.
Figure 3B:
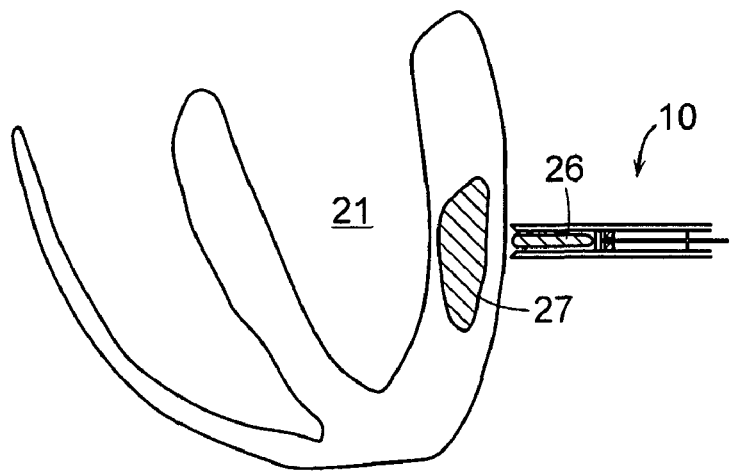
FIGS. 3B through 3D provide illustrations of a method of implanting myocardial tissue into a treatment area using a rigid device in accordance with the present invention.
Figure 3C:
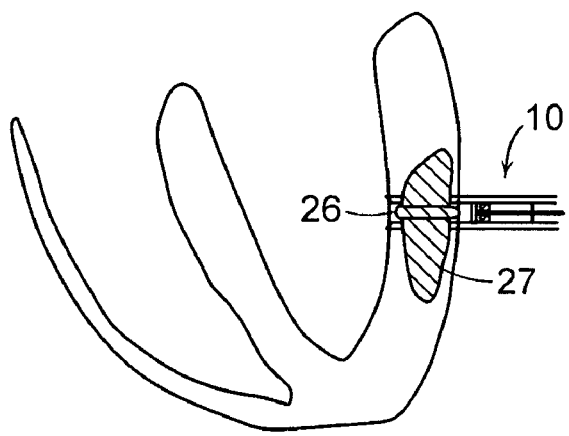
Figure 3D:
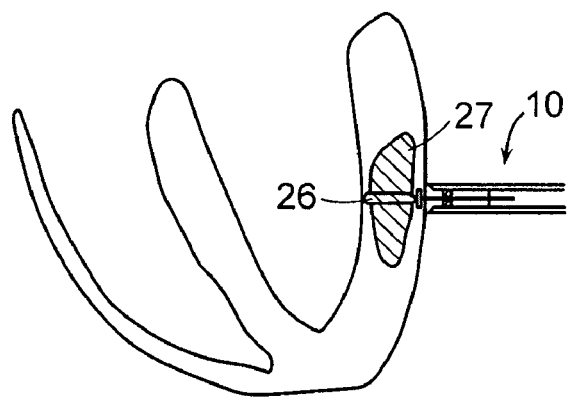

In FIG. 3A, the myocardium 25 includes a treatment area 27, e.g., a myocardial infarct scar or ischemic myocardial tissue, in the wall 24b of the left ventricle 21. As shown in FIGS. 3B-3D, after the device 10 is properly positioned with respect to the treatment area 27, the razor-sharp edges 11 of the device 10, e.g., a cutting cannula, puncture the treatment area 27; the hollow tube 12 is introduced into the treatment area 27; and the distal tip 13 of the hollow tube 12 is advanced to a discrete depth.

Once the distal tip 13 of the device 10 is positioned at the desired depth, the hollow tube 12 can be withdrawn from the treatment area. As the hollow tube 12 is being withdrawn, the shaft 18 of the stylet 20 is controlled to maintain the stylet 20 and, more particularly, the front portion 15 of the stylet 20 stationary or substantially stationary. As a result, as the hollow tube 12 is progressively withdrawn from the treatment area 27, the front portion 15 of the stylet 20 progressively extrudes the myocardial tissue sample 26, leaving the myocardial tissue 26 in the treatment area 27 of the wall 24b of the left ventricle 21.

Figure 3E:
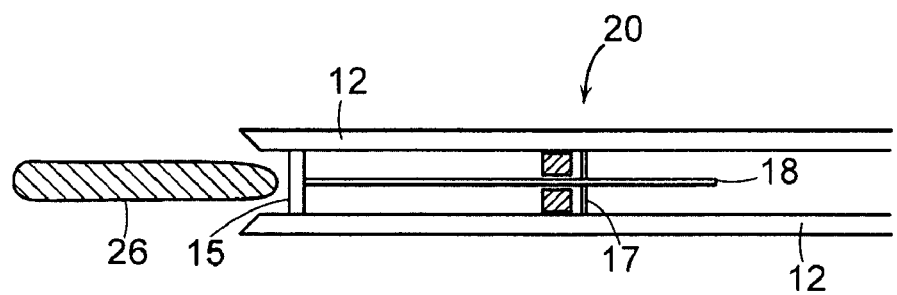
FIG. 3E provides an illustrative embodiment of a retrieval and implantation device during an implantation stroke.

FIG. 3E provides an illustrative diagram of the implant stroke of the device 10. Particularly, after insertion into the treatment area 27, the hollow tube 12 is progressively withdrawn from the treatment area 27 and the front portion 15 of the stylet 20 remains stationary or substantially stationary. As a result, the myocardial tissue 26 also is extruded into the treatment area 27. Once the stopping device 16 and rear portion 17 make contact, further movement of the stylet 20 is arrested and the desired volume of myocardial biopsy tissue 26 has been implanted in the treatment area 27.

Having described methods of taking and implanting myocardial tissue 26 using a rigid surgical device, methods of taking and implanting myocardial tissue 26 using a catheter-based system will be described. Referring to FIG. 4B, preferably, the catheter-based device 40 comprises a small, rigid tube 48 that is structured and arranged at the distal end 43 of a percutenous flexible shaft 42 that can be made using a plastic sheath or a shaped memory material such as nitinol.

In a preferred embodiment, during sampling or intake, a multi-purpose catheter or similar device can be positioned at or near the basal septum. For example, using fluoroscopic and/or echocardiographic guidance, the multi-purpose catheter can be inserted in the internal jugular vein and advanced until it is properly positioned on the basal septum. Those skilled in the art can appreciate that other points of access to the basal septum are possible and each is included herein.

Once the multi-purpose catheter is properly positioned, a hypotube assembly 40 comprising a percutenous flexible shaft 42 and a rigid tube 48 structured and arranged at its distal end 43. The sharp distal edge 41 of the tube 48 is pressed into the septum to obtain intact myocardial tissue sample 46. As the sharp edge 41 advance further into the septum, the myocardial tissue 46 enters the distal end 43 of the hollow tube 48, displacing the stylet 20 by pushing against the front portion 45. Once the front portion 45 displaces a discrete distance, e.g., one (1) cm, from the distal end 43 of the rigid tube 48, the rigid tube 48, including the myocardial tissue 46, can be removed. In a preferred embodiment, a location on the septal wall is chosen where the thickness of the wall corresponds to the length of the sample being obtained. In this case, the sampling tube penetrates through the wall, thereby obviating the need to cut or tear the end of the sample from the site. Alternatively, the sampling device can include a cutting tool or edge to sever the sample from the remaining tissue.

Figure 4A:
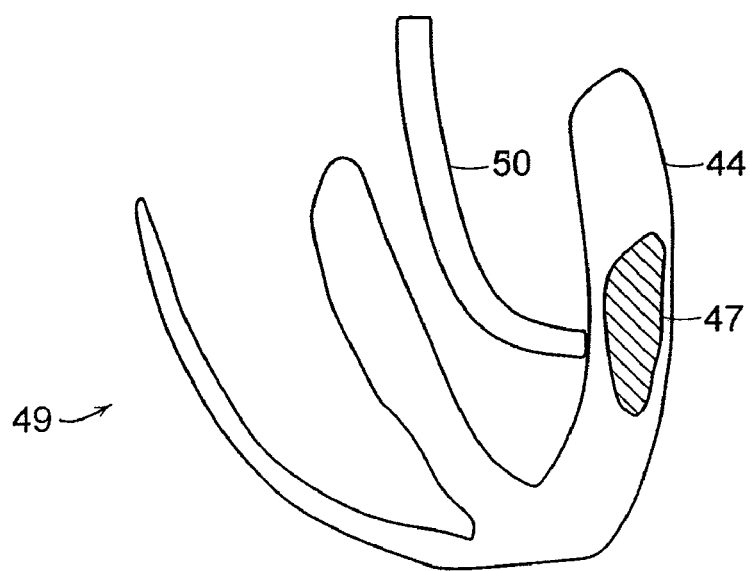
FIG. 4A provides a diagram of a human myocardium with a treatment area.
Figure 4B:
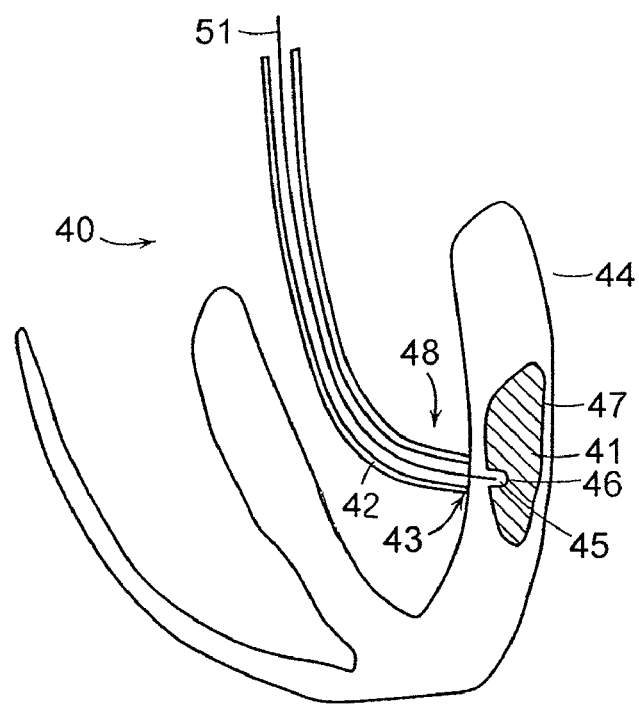
FIG. 4B provides an illustration of a method of implanting myocardial tissue into a treatment area using a catheter-based device in accordance with the present invention.

Referring to FIGS. 4A and 4B, the step of implanting the myocardial tissue 46 in a second region of the mammalian organ using a percutenous flexible shaft 42 with a rigid tube 48 will be described. Preferably, the hypotube assembly 40 delivers the myocardial tissue 46 to the treatment area 47, for example, a myocardial infarct scar or ischemic myocardial tissue, epicardially. As previously mentioned, the embodied method obviates an intermediate, cellular alteration, i.e., cell culturing, step.

In FIG. 4A, the myocardium 49 includes a treatment area 47 in the free wall 44. In one aspect of the present embodiment, a guiding catheter is first introduced into the myocardium 49, e.g., through the femoral artery 50, and positioned at the treatment area 47. Fluoroscopic and/or echocardiographic guidance of the guiding catheter can be used as necessary. A hypotube assembly 40 is then introduced into the left ventricle through a guiding catheter.

The sharp edges 41 of the rigid tube 10 puncture the treatment area 47 the hollow tube 48 is introduced into the treatment area 47 and the distal tip 43 is advanced to a discrete depth. Once the hollow tube 48 is positioned at the desired depth, the hollow tube 48 can be withdrawn from the treatment area 47.

As the hollow tube 48 is progressively withdrawn, the shaft 51 of the stylet 20 is controlled to maintain the stylet 20 and, more particularly, the front portion 45 of the stylet 20 stationary or substantially stationary. As a result, as the hollow tube 48 is progressively withdrawn, the front portion 45 of the stylet 20 progressively extrudes the myocardial biopsy tissue 46, leaving the myocardial tissue 46 in the treatment area 47 of the free wall 44 of the left ventricle.

The embodied transplantation method can also be used to increase or enhance cellular growth in a region of injured mammalian myocardial tissue and/or to improve cardiac function in a mammalian subject having an injured myocardium. Similarly, the embodied transplantation device can be used to retrieve a tissue sample from a donor area for implantation in a portion of a myocardium without cellular alteration of the sample to repair an injured myocardial region.

To measure the effectiveness of the procedure, thirteen 30-40 kg Yorkshire pigs were anesthesized with intramuscular ketamine (10 mg/kg) and isofluorane inhalation anesthesia. Right femoral artery was exposed via a surgical cutdown under sterile conditions and a 6 Fr arterial sheath (Cordis, Miami, Fla.) was inserted. Heparin was administered (100 IU/kg IV). Left coronary cardiac catherization was performed and a 6 Fr Hockeystick guiding catheter (Cordis) was positioned in the left main coronary artery. A 0.014" guide wire was advanced to left anterior coronary artery (LAD) and a 2.75 mm×20 mm angioplasty balloon (Maverick balloon, Guidant) was placed in the mid LAD past the take off of first diagonal branch 1 (D1) and inflated for 60 minutes to produce an anterior myocardial infarction. The location was confirmed in both right anterior oblique (30% RAO) and left anterior oblique (60% LAO) views. Ventricular fibrillation was terminated with external defibrillation and sustained ventricular ectopy was suppressed with boluses and drips of lidocaine (100 mg IV), amiodarone (75-150 mg IV) and magnesium sulfate (2-4 g IV). EKG was monitored for ST elevations. Balloon was deflated at 60 minutes and removed.

Cardiomyoplasties were performed in the acute setting of the infarction. Right anterior thoracotomy through the $4^{th}$ intercostal space was performed, the pericardium was opened and the lung retracted. Right ventricular wall was incised and a short 8 Fr sheath (Cordis) was inserted, and secured with a purse string suture. A bioptome (Cook Inc, Bloomington, Ind.) was inserted via the 8 Fr sheath into the RV and aimed at the septum under fluoroscopic guidance. Between 6 and 10 sample cores (average of 9) were obtained with the liver bioptome device from the right ventricular septum. In this embodiment a separate injection device is used. The samples were then transferred into a microtweezer injection device (16-gauge needle with retractable microtweezers—supply drawing?). Seven animals were randomized to myotissue injections whereas the other 6 controls received sham injections. The animals were then allowed to recover for 4 weeks.

The animals underwent MRI on a 1.5 T General Electric TwinSpeed Scanner (GE Healthcare Technologies, Milwaukee, Wis.) 4 weeks after infarction. The following measurements were performed: 1). extent of myocardial necrosis defined as areas of myocardium showing thinning, absent wall motion and no contrast uptake on perfusion imaging, 2). resting left ventricular ejection fraction (EF), and 3). to assess myocardial perfusion using magnetic resonance first-pass perfusion analysis, and 4). myocardial infarction volume as assessed by delayed enhancement imaging.

The animals were placed in the right antecubital position, and a phased-array cardiac coil was placed around the chest. Mechanical ventilation and gaseous anesthesia was continued during scanning. Scout images were obtained to determine the short and long axis views of the heart. Using the fast imaging employing steady-state acquisition (FIESTA) pulse sequence assessed global LV function. Short axis cine images were acquired with ECG gated and without breath hold. The heart was imaged from base to apex with eight to ten LV short axis slices. The image parameters were as follows: TR/TE=3.8/1.7 ms, flip angle was 45°, 224×224 matrix, 8 mm slice thickness no gap, bandwidth 125 kHz, field of view 26 cm and 1 NEX.

MR Perfusion images were acquired in three slices each matched to short axis cine slice, representing the basal, mid-ventricular, and apical myocardial segments, with ECG gated and a non-breathhold fast gradient echo-echo train with multi phase (FGRET-MP) pulse sequence. After three to five heart beat initiation of the sequence as the baseline images, first-pass perfusion images were acquired after intravenous injection of 0.1 mmol/kg bodyweight gadolinium-DTPA (Magnevist, Berlex Laboratories, N.J.) which was injected at the rate of 3.0 ml/sec, followed by a 20 ml saline flush at the rate of 3.0 ml/sec by an infusion pump, total 50 phases were acquired each slice. Imaging parameters included the following: TR/TE=9.3/1.8 ms, inversion time 160 ms, echo train length of four, 128×128 matrix, flip angle 25°, 26 cm field of view, 8 mm slice thickness, 2 mm section spacing, 125 kHz bandwidth.

Infarct size was analyzed by using the delayed-enhancement MRI technique. Images were acquired 15 min after first-pass perfusion imaging. By using an ECG-gated, non-breathhold, 2D interleaved, inversion recovery, fast-gradient recoiled echo pulse sequence. A total of 8-10 continuous short-axis slices were prescribed to cover the entire LV from base to apex. Imaging parameters were as follows: TR/TE=6.7/3.2 ms, inversion recovery time 180~220 ms, flip angle=20°, 256×192 matrix, 8 mm slice thickness/no gap, bandwidth 31.25 kHz, 26 cm field of view and 2 NEX. Inversion recovery time was adjusted as needed to null the normal myocardium.

All the measurements were analyzed offline by independent blinded investigator with commercial software (MASS Analysis, General Electric). For the myocardial perfusion analysis, short axis images were sorted according to slice position and acquisition time, the LV endocardial and epicardial contours were draw manually and six equiangular segments (anterior, antero-lateral, inferior, infero-septal, antero-septal) per slice were generated automatically, the anterior septal insertion of the right ventricle as a reference point. The upslopes of the myocardial signal in six segments were divided by the upslope of the signal in the left ventricular cavity, which was regarded as a measure of the input function.

LV pressure was measured with a high fidelity micromanometer catheter placed into the LV in a retrograde fashion. The rate of change of LV pressure was measured and averaged over 10 beats (dP/dt). All data was recorded digitally and stored for off-line analysis (Sonosoft from Sonometrics Corporation, Ontario Canada).

Four weeks after infarction and treatment, animals were sacrificed with lethal injection of pentobarbital. At the end of the experiment the hearts were harvested and cut into 5 standardized slices. The apical and the middle slice were taken for staining with 1% TTC in phosphate buffer (Sigma Chemical). The heart slices were incubated for 20 minutes at 38 degrees C. Stained slices were placed on clear acetate glass and the infarct area was measure by planimetry. Remaining cardiac muscle tissue was placed in 10% formalin in buffered saline for paraffin embedding and hematoxyline and eosin staining. Tissue was also snap frozen in liquid nitrogen at −80 degrees C. for subsequent protein analysis (for VEGF, FGF-2 TGF-beta, and PECAM-1 protein expression).

Myocardial cells were lysed by RIPA solution (Boston Bioproducts; Ashland, Mass.) and fractionated by 10% SDS-polyacrylamide gels. Protein extracts were transferred to polyvinylidene difluoride membranes (Millipore; Bedford, Mass.). VEGF, FGF-2, TGF-beta and PECAM-1 were detected with their respectively specific antibodies (Santa Cruz Biotechnology, CA). Immunoblots were visualized by enhanced chemiluminescence Western blotting detection reagents (Amersham Life Science; Arlington Heights, Ill.). All values of image densitometry studies were quantitated by ImageQuant software and adjusted by sample loading.

Data analysis and graphing was performed using Statview software package. Groups were compared using two-tailed student t-test with p-value cut off for statistical significance of 0.05. Normal distribution of the data was verified before performing parametric analysis. Appropriate correction was made for multiple comparisons.

The initial creation of the myocardial infarction method with balloon occlusion was associated with less than 20% mortality secondary to ventricular fibrillation during balloon occlusion. There was no additional mortality associated with the implantation procedure. The animals tolerated both the sample removal of the right ventricular septum and the anterior wall implantation without hypotension or sustanined arrhythmia. The engrafted tissue remained viable as shown by subsequent histological and morphometric evaluation at 4 weeks post-implantation.

Figure 5B:
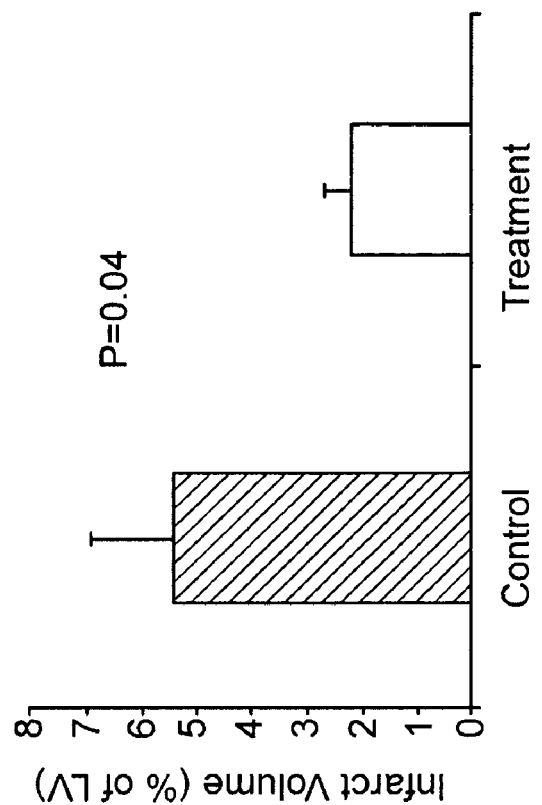
FIG. 5B illustrates the improvement in infarct volume of treated animals measured by MRI.
Figure 5A:
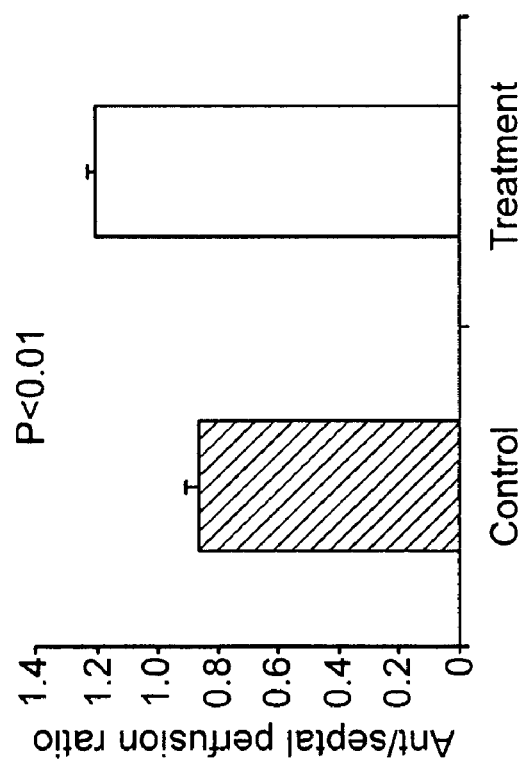
FIG. 5A illustrates the ratio of anterior wall to septal wall myocardial perfusion measured by MRI.

The LV myocardium was divided into six equiangular segments per slice. For each slice, perfusion in anterior wall, anteroseptal wall, and lateral wall were measured by MR first-pass perfusion based on the maximal upslope of myocardial signal intensity enhancement versus time. The ratio of perfusion in the treated anterior wall to untreated septal wall was 1.2±0.12 in the treated animals versus 0.86±0.05 in controls (p<0.01). Namely, perfusion was greater in the anterior wall in treated animals than in control animals but it did not differ in the septal area where no treatment was applied. The results are illustrated in FIG. 5A. Differences in perfusion as assessed by MRI correlated with global assessment of myocardial function as well as infarct volume measurements.

Mean volumes of myocardial infarct as measured by delayed enhancement on MRI were 2.2±1.5 ml versus 5.42±0.5 ml in the treated versus control animals (p=0.04; FIG. 5B) indicating that myotissue transplantation decreased infarction size. Measurements were made in the same slice of the myocardium that was used to assess perfusion.

Figure 8A:
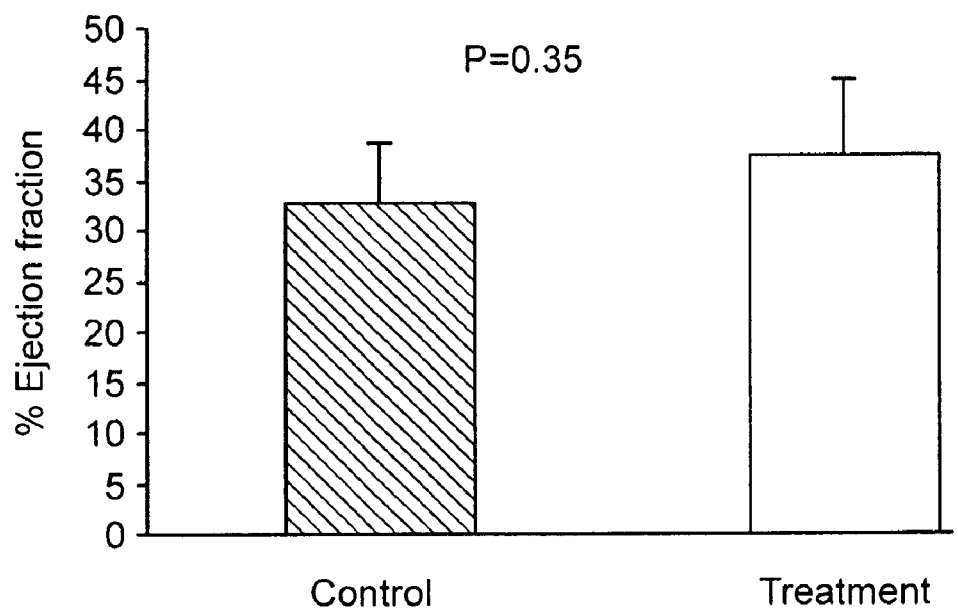
FIG. 8A illustrates the improvement in ejection fraction as measured with MRI.

Percent wall thickening was six-fold greater in the anterior wall of the treated animals than in their untreated counterparts with the result reaching statistical significance (p=0.069) (FIGS. 6A and 6B). No such difference was seen in the non-implanted septum (p=0.4). Concomitantly, the wall motion score tended to increase in the anterior wall of the implanted animals compared to the controls (p=0.17), as well as the septum likely due to translation of the improved contractility in the adjacent anterior wall (FIGS. 7A and 7B). The difference in the overall ejection fraction between the two groups (32% vs 37%; p=0.35) did not reach statistical significance (FIG. 8A).

Figure 8B:
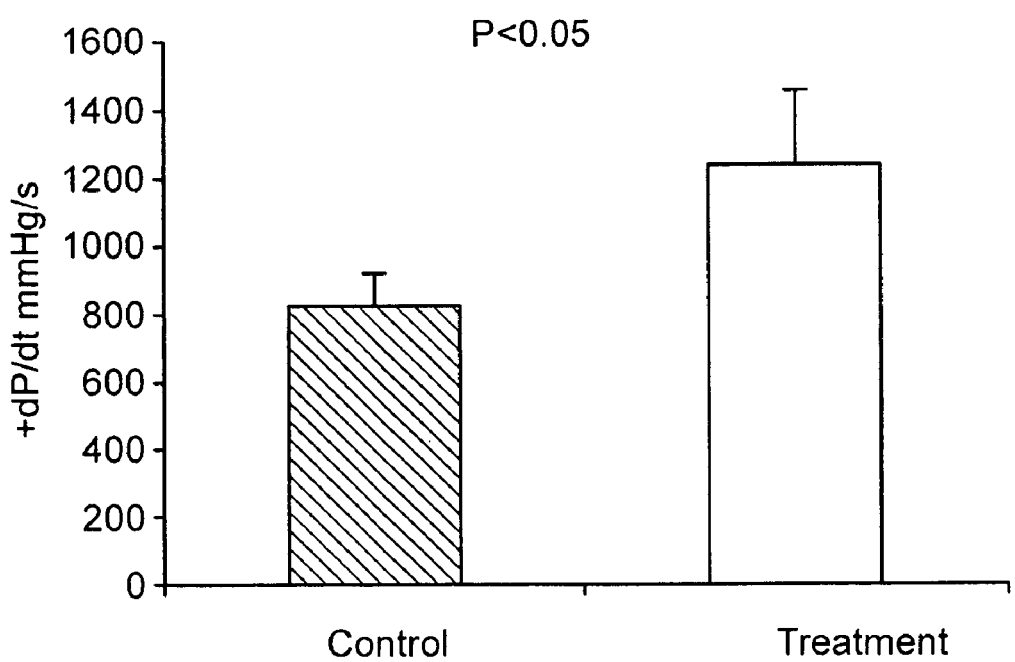
FIG. 8B illustrates the improvement in contractility in treated animals measured by micromanometer catheter.

Contractility as measured by maximal dP/dt was 1295±215 mmHg/s in the treated group and 817±91 mmHg/s in the control group (p<0.05) indicating that the overall systolic myocardial function improved in the treated animals (FIG. 8B) in agreement with the percent anterior wall thickening MRI results.

Figure 9B:
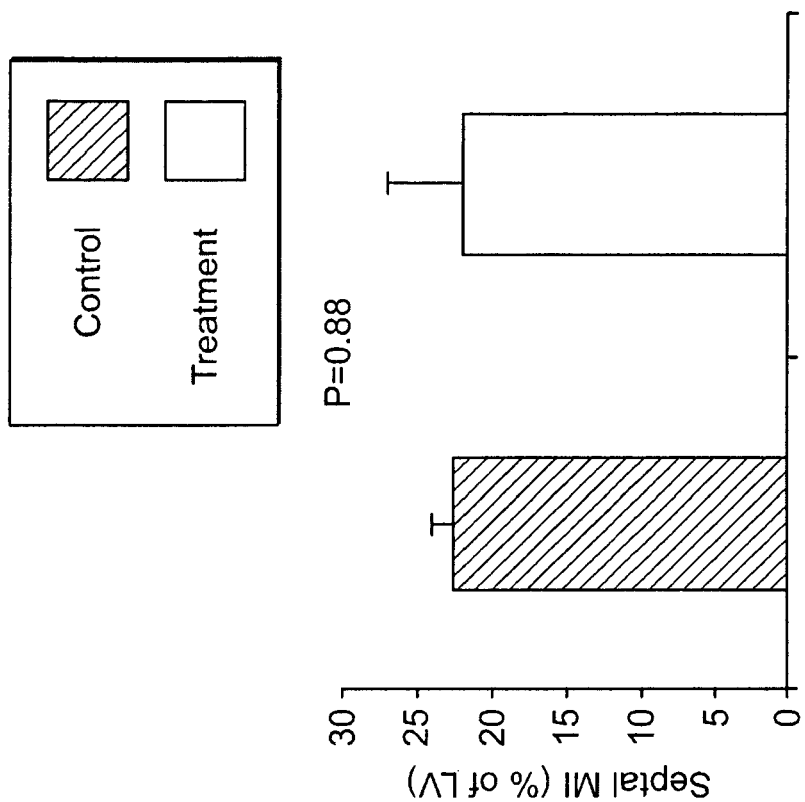
FIGS. 9A and 9B show changes in infarct size in the anterior and septal wall, respectively, as measured by TTC staining.
Figure 9A:
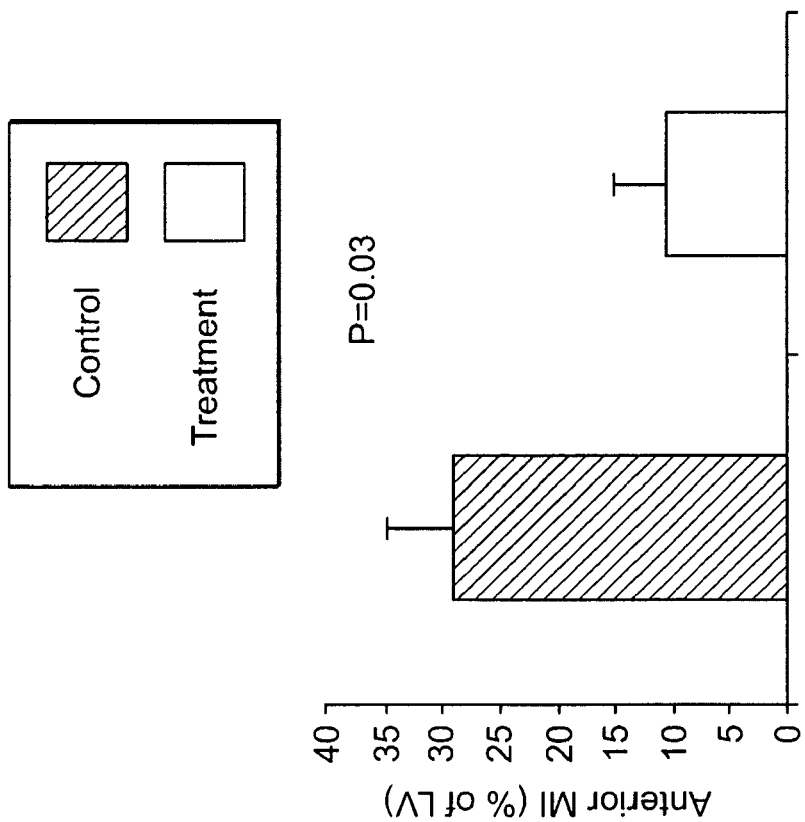
Figure 10A:
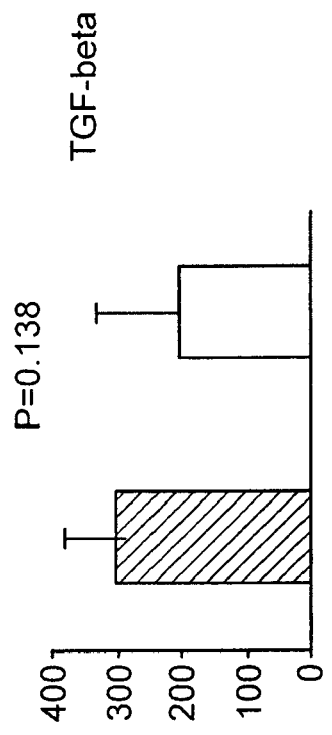
FIGS. 10A-10D shows changes in angiogenic and anti-apoptotic protein expression in untreated and treated animals.
Figure 10C:
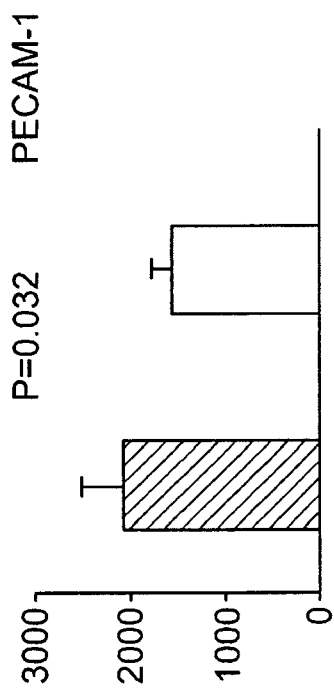
Figure 10B:
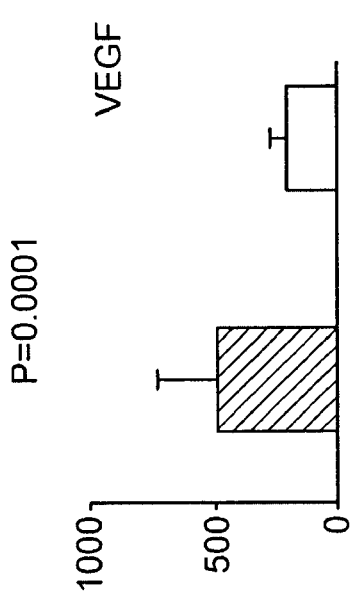
Figure 10D:
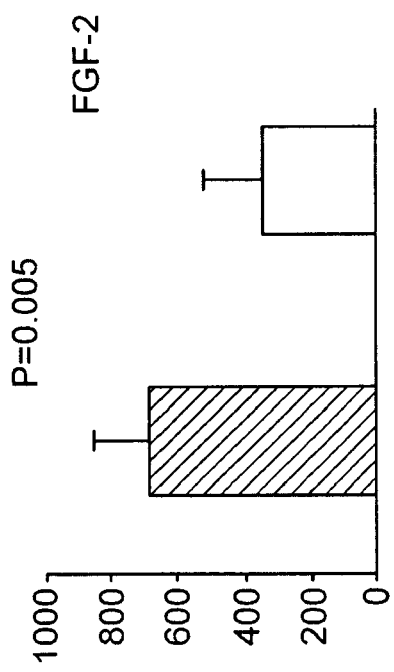

Morphometric measurement of myocardial infarction size by TTC was done to determine the effect of myotissue transplantation on infarct size. Infarct size was controlled by positioning the balloon in the mid LAD (past D1) during each procedure and maintaining inflation for 60 minutes. Despite standardizing the procedure, infarct size varied somewhat between animals due to anatomic variation. Since one can not control exactly the infarct size between the animals, the size of anterior wall infarct was normalized to the size of septal infarct, as anterior wall infarction was treated whereas the septum was not, septal infarct size served as internal control for each animal. To account for the animal to animal infarct size difference and isolate the effect of myotissue transplantation on the anterior wall we compared the percent anterior wall to septal infarct size (FIGS. 9A and 9B). There was a significant difference in infarct size between untreated and treated animals. The percent infarct size of the anterior wall area in the treated animals was 11±4.5% vs 29±5% in untreated animals (p=0.03). There was no difference between the two groups in percent infarct size of the septal area (21% vs 22%; p=0.88).

In order to explore the mechanisms underlying improvement in perfusion and myocardial function due to cardiomyoplasty, histopathological and protein expression analysis were performed on infarcted myocardium. Levels of VEGF, FGF-2, and PECAM-1 protein were significantly lower in treated animals. In addition, levels of TGF-beta tended to be lower in the infarcted anterior wall of treated animals compared to the non-infarcted zone. Densitometry measurements from Western blots are shown in FIGS. 10A-10D.

Described herein is a safe, effective and simple method of performing cardiomyoplasty with the entire intact autologous myocardial tissue that obviates the need for cell culture with its potential complications of infection and decreased survival of cells. This approach can be implemented with relative ease during planned revascularization procedure such as coronary artery bypass grafting (CABG).

More importantly, implantation of the whole tissue biopsy avoids cell shearing and preserves intact tissue architecture as well as the natural cytokine and growth factor milieu within the extracellular matrix scaffold. It is possible that improvement in perfusion observed locally in the anterior wall that was treated with cardiomyoplasty is due to the growth factor secretion from the extracellular matrix of the implants. Our Western blot analysis, however, showed decreased levels of angiogenic factor expression (VEGF, FGF-2) within the infarct zone as the LV function normalized. The tissue was harvested 4 weeks post-implantation. The levels, thus reflected, a completed repair process and neovascularization in the treated group. Cardiac stem cells may be contained within the biopsy tissue and may be able to differentiate into arterioles, and provide enough of a regenerative potential that the need for elaboration of high levels of angiogenic proteins by the infarct zone is partly decreased. The endothelial cells contained within the tissue sample may be capable of migrating to the epicardial coronary vessels and repairing the endothelium thereby contributing to improved perfusion and improved endothelial function.

It has been documented that stem cells and myocyte cell implantation does not result in synchronously beating new cardiomyocyte formation but rather improves myocardial function globally by positively affecting the remodeling process in the adjacent regions in addition to the implantation site. The decreased infarct volume in treated animals compared to untreated ones implies that the process of myocardial regeneration has taken place. Implantation of cardiomyocytes with extracellular matrix milieu and growth factors are better than when individual cells are injected into the unfavorable milieu of the scar. This cardiomyoplasty technique resulted in a global improvement in myocardial function as evidenced by increased peak contractility (dP/dt) on hemodynamic measurements likely deriving from decreased filling pressures and wall tension. The present MRI measurements show improvement in both perfusion and a decrease in the infarct volume within the treated anterior wall. In addition, the percent thickening of the implanted anterior wall was improved in the treated animals compared to the untreated ones, as was the wall motion score. This indicates a direct contribution of the implant to the anterior wall contractility. The improvement in contractility in the untreated adjacent septum was not statistically significant, and the slight trend to improvement in the wall motion score was likely due to the translated motion of the anterior wall. The magnitude of difference in the ejection fraction was not statistically significant, likely due to low number of animals and individual animal variability. The functional analysis results were also confirmed by morphometric analysis with TTC staining and demonstrated that infarct size was smaller in the treated anterior wall compared to the untreated septum. Histological analysis confirmed the viability of transplanted tissue at 4 weeks after implantation.

There is a comparison of the infarct volumes by MRI in the implanted and sham operated groups. The infarct size as normalized by septal infarct size was not different in the two groups. Infarct volumes were 40% lower in treated animals.

To measure the effect of the removal and implant procedure on tissue two weeks after infarction twelve Yorkshire pigs were anesthetized and a 6 Fr arterial sheath was inserted in the femoral artery for the purpose of introducing an angioplasty balloon in the left anterior coronary artery. The balloon was inflated for 60 minutes to produce an anterior myocardial infarction.

Ventricle fibrillation was terminated and external defibrillation and sustained ventricular ectopy was suppressed with boluses and drips of lidocaine, amiodarone, and magnesium sulfate. Balloons were deflated at 60 minutes and removed. The animals were allowed to recover for two (2) weeks, after which cardiomyoplasties as described herein were performed, which is to say, that the right ventricle wall was incised and a short 8 Fr sheath was inserted. A bioptome was inserted into the right ventricle via the 8 Fr sheath, aimed at the septum.

Between six and ten samples were obtained from the right ventricle septum and the samples were implanted into the anterior wall of the left ventricle about 0.5 cm from the left anterior coronary artery and the D1/D2 bifurcation.

Two weeks after myocardial infarction and at the time of cardiomyoplasty baseline echocardiography was performed to assess for any changes in left ventricle ejection fraction and regional wall motion, and left ventricle end diastolic dimension. Recordings of two-dimensional echocardiography were performed from the left parasternal axis windows with the animal in a supine position.

End systolic (ES) and end diastolic (ED) left ventricle cavity diameters at the level of midpapillary muscles were determined in the M-mode. Ejection fraction was calculated using the equation:

$$(ED_{volume} - ES_{volume})/ED_{volume} \times 100.$$

Wall motion abnormalities were assessed in short parasternal axis views. In order to visualize the apex, which was affected by the infarct, epicardial echocardiography was also performed at the time of the thoracotomy and standard epicardial views were obtained. Measurements were repeated at four (4) weeks post-infarction at the time of organ harvest.

Left ventricle pressure was measured with a high fidelity micromanometer catheter placed into the left ventricle in a retrograde fashion. The rate of change of left ventricle pressure was measured and averaged over 10 beats (dP/dt). All data were recorded digitally and stored for off-line analysis as previously described.

Left atrial pressures were measured with a 3.5 JL 5F catheter and also recorded on Sonosoft software. These measurements were obtained at the time of the implantation two (2) weeks after the initial myocardial infarction as well as at the time of harvest at four (4) weeks after the myocardial infarction.

At the end of the experiment the hearts were harvested and cut into five (5) standardized slices. The apical and the middle slice were taken for staining with 1% triphenyl tetrazolium chloride (TTC) in phosphate buffer. The heart slices were incubated for 20 minutes at 38° C. Stained slices were placed on clear acetate glass and the infarct area was measure by planimetry. More specifically, two independent observers measured the infarct area and the results were subjected to statistical analysis.

Remaining cardiac muscle tissue was placed in 10% formalin in buffered saline for paraffin embedding and hematoxyline and eosine staining, as well as trichrome staining. Tissue was also snap frozen in liquid nitrogen at −80° C. for subsequent protein analysis, e.g., VEGF, FGF-2, PECAM and anti-apoptotic protein IAP-2 staining, and matrix metalloproteinase expresion. The animals were sacrificed with lethal injection of pentobarbital.

Myocardial cells were lysed by RIP A solution and fractionated by 10% SDS-polyacrylamide gels. Protein extracts were transferred to polyvinylidene difluoride membranes. VEGF, FGF-2, IAP-20 and PECAM were detected with their respectively specific antibodies. Immunoblots were visualized by enhanced chemiluminescence Western blotting detection reagents.

All values of image densitometry studies were quantified by ImageQuant software and adjusted by the ratio of sample loading by Ponceau Red staining and normalized to the infarct size.

Paraffin tissues were subjected to the antigen retrieval techniques, i.e., immersion in boiling citrate buffer. Immunohistochemistry was performed using anti-sca-l at 1:250 dilution, mdr-l at 1:40 dilution, and c-kit at 1:200 dilution. Anti-isotype secondary antibodies (dilution 1:250) and streptavidin-biotin system with diaminoxybenzidine development system was used to visualize the primitive stem cells. Sections were counterstained with hematoxyline and coverslipped.

Cells were counted using image analysis software, e.g., SpotAdvanced. Cells were counted in several representative 10× power fields in each animal. Data are presented as the average number of cells per 10× power field.

Data analysis and graphing were performed using the Statview software package. Groups were compared using two-tailed student t-test with p-value cut-off for statistical significance of 0.05. Normal distribution of the data was verified before performing parametric analysis. Appropriate correction was made for multiple comparisons. Data are expressed as means with standard deviations with the exception of TTC staining data where standard error was used given that two separate measurements were made per animal and treated as individual samples. Similar analysis was performed in an acute model of myocardial infarction.

The initial creation of the myocardial infarction with balloon occlusion was associated with 20-30% mortality secondary to ventricular fibrillation during the balloon occlusion. There was no additional mortality associated with the cardiomyoplasty procedure. The animals tolerated both the biopsy of the right ventricle septum and the anterior wall implantation well without hypotension or arrhythmia. The engraftment was approaching 100% as shown by subsequent histological and morphometric evaluation at four (4) weeks post-implantation.

Figure 11A:
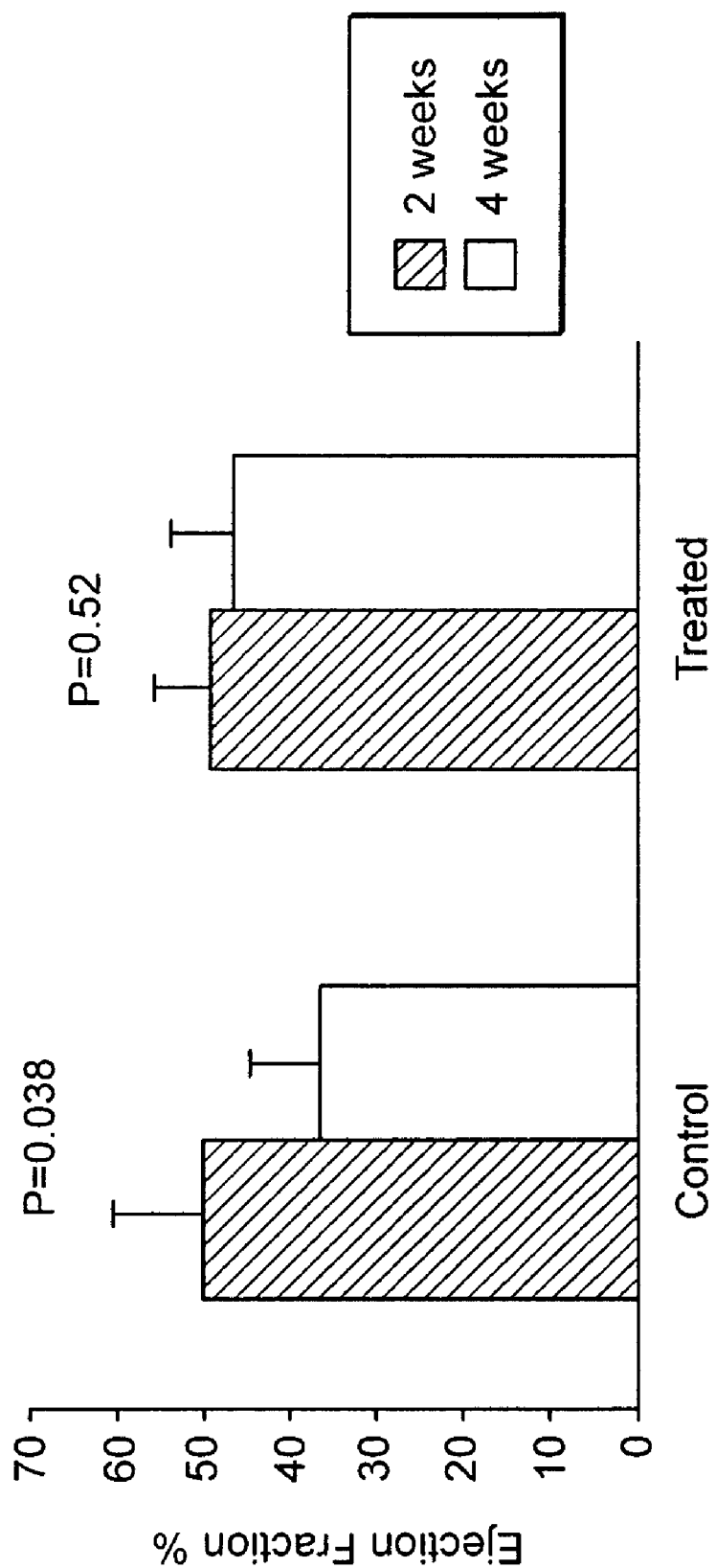
FIG. 11A illustrates the prevention of deterioration in ejection fraction in treated subjects at two and four following myocardial infarction.

Animals treated with myotissue maintained the same ejection fraction at two (2) and four (4) weeks post-infarction (49%±6.5% vs. 46%±7.4%; p=0.52). In contrast, as shown in FIG. 11A, ejection fraction decreased significantly in untreated animals (50%±10.4% vs. 36%±8.7%; p=0.038). This indicated that myotissue implantation prevented unfavorable changes that ensue after myocardial infarction.

Figure 11C:
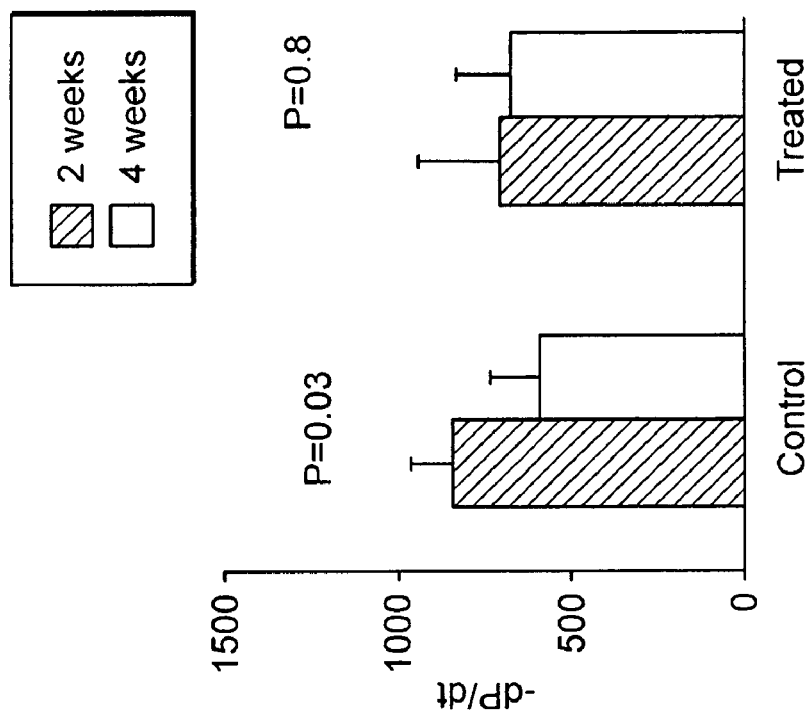
FIGS. 11B and 11C show the hemadynamic assessment of contractility and relaxation, respectively.
Figure 11B:
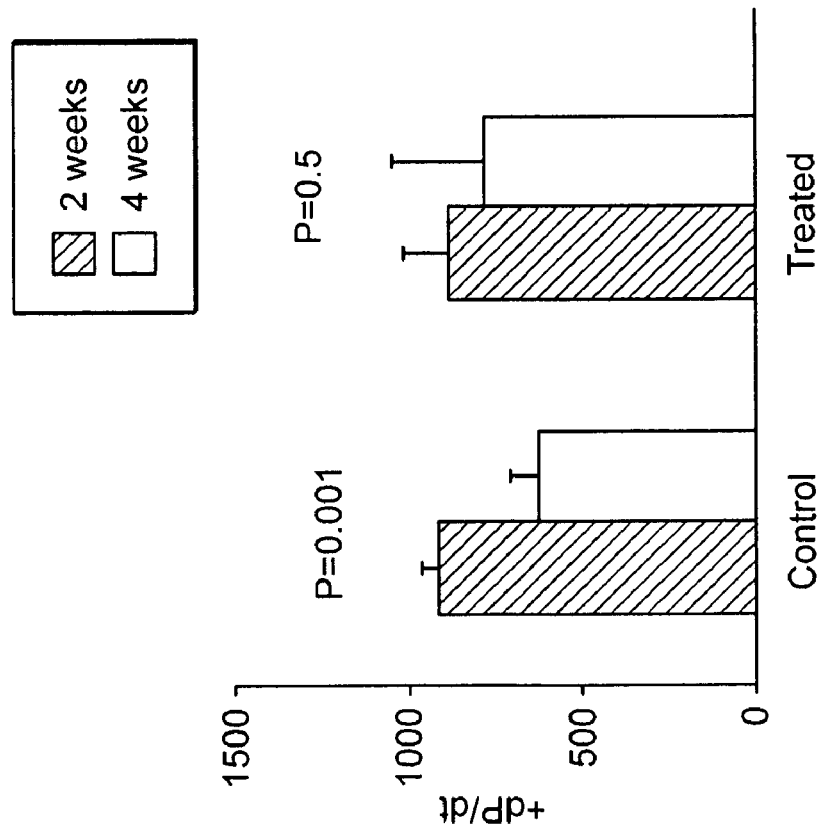
Figure 11D:
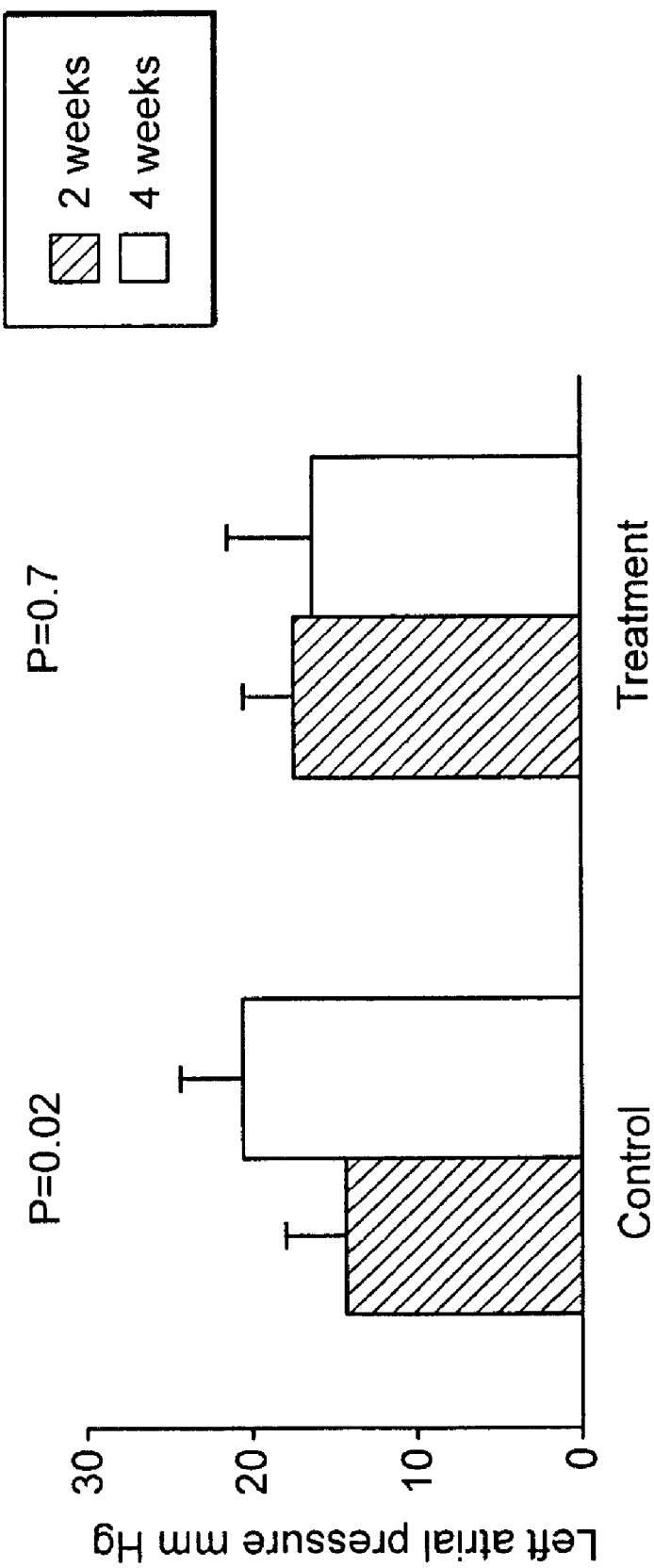
FIG. 11D shows the left atrial pressure remains normal in treated subjects and is elevated at four weeks in untreated subjects.

Hemodynamic assessment results paralleled the echo results in that both systolic (positive dP/dt) and diastolic (negative dP/dt) function, as well as filling pressures did not change in the treated animals between weeks two (2) and four (4) post-infarction (FIGS. 11B, 11C and 11D, respectively). The left atrial pressures were 17 versus 16 (p=NS), dP/dt was 874 versus 763 (p=NS) and negative dP/dt was 716 versus 676 (p=NS).

The untreated control animals on the other hand, have significantly decreased positive dP/dt (906 down to 609; p=0.009) and negative dP/dt (850 down to 599; p=0.0332). They also have increased left atrial pressures (14 up to 20; p=0.0169). This again was indicative of the role of myotissue in preventing the decline in left ventricular function that ensues after myocardial infarction.

Morphometric measurement of myocardial infarction size by TTC was done to confirm the effect of cardiomyoplasty on infarct size reduction. As previously described, the infarction size was controlled by positioning the balloon in the mid-left anterior coronary artery (past diagonal branch 1) during each procedure and maintaining inflation for 60 minutes. This, however, was subject to some variability between animals.

This variability and average infarct size was no different between animal groups at two weeks post-infarction before randomization as measured by echocardiography, e.g., ejection fraction was 50% and 49% in the two groups; p=NS. There was a significant difference in infarct size between untreated controls and animals that received cardiomyoplasty treatment. The percent infarct size in the anterior wall of treated animals was significantly smaller than in the control animals (21.4%±3.3% versus 33.4%±2.2%; p=0.006) as shown in FIG. 12A. Unlike in the acute myocardial infarction model, there was also a significant difference in the infarct size in the untreated septum (16.2%±3.3% and 27.1%±3%; p-value=0.024) as shown in FIG. 12B, indicating a global effect of myotissue on myocardial regeneration. TTC staining assessment was consistent between two independent observers (corr. coeff=0.82; p=0.0005).

Histological analysis by H&E (hematoxylin-easin) and trichrome staining confirmed the presence of extensive areas of infarction and fibrosis in the anteroseptal area. In the treated animals viable implants could be seen present in multiple tissue sections.

Adjacent to the implants and within the infarct region markedly increased numbers of primitive stem cells positive for mdr-1 were seen. These cells were not as numerous in the untreated control animals (9+6.2 vs. 17+3.9 mean number of cells per 10× power field; p=0.038). Numbers of sca-1 cells were not significantly different between the two groups (13+13 vs. 16+25; p=0.84). C-kiH stem cells on the other hand were more numerous in the control (untreated) animals (7.8+6 vs. 0.6+1.3; p=0.034).

Figure 13:
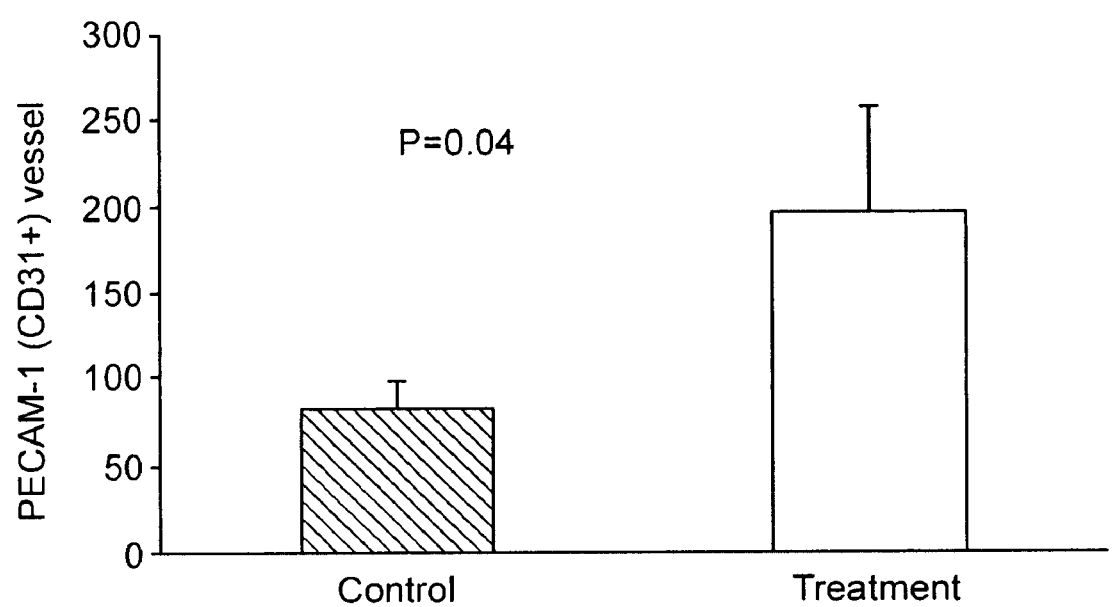
FIG. 13 illustrates the three-fold increase in the number of vessels in treated subjects.

Accordingly, it can be inferred from this result that mdr-1 positive and possibly sca-1 positive adult cardiac stem cells were potentially originating and migrating into the infarct region from the implants. This is in contrast to the trafficking of cardiac progenitors from the bone marrow after infarction, which may be responsible for increased number of c-kih progenitor cells in the untreated animals. PECAM-1 staining indicated an increase in the number of capillaries and new-vessels in treated animals (FIG. 13).

Figure 14A:
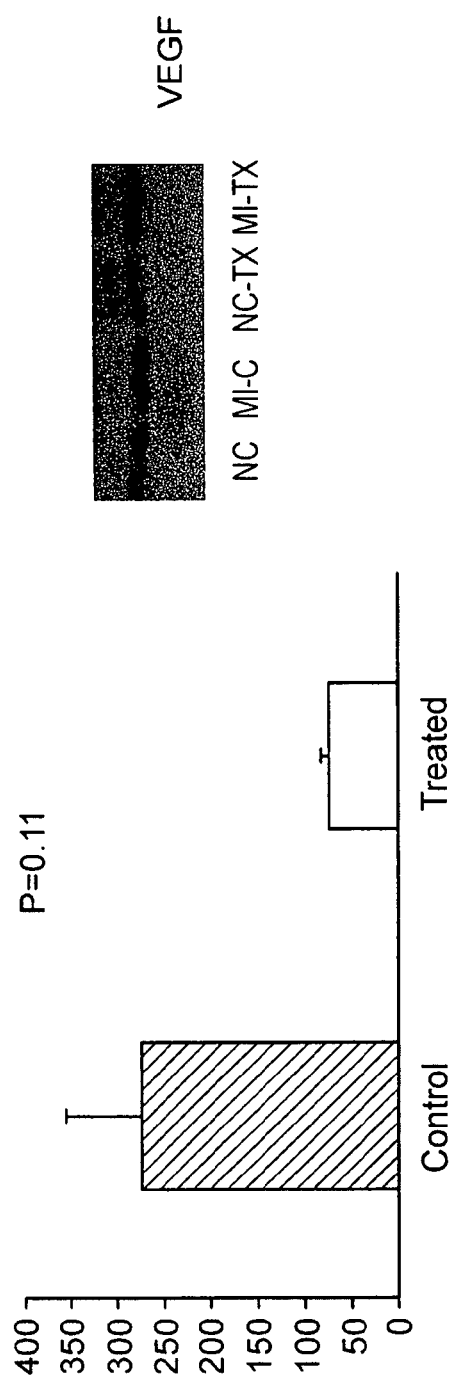
FIGS. 14A and 14B show the levels of angiogenic factors in VEGF and GDF-2, respectively.

In order to explore whether the improvement in myocardial function due to cardiomyoplasty is mediated by neo-angiogenesis, protein expression analysis of infarcted myocardium was performed. Levels of VEGF-2 (23 kDa) protein tended to be two-fold lower in the treated animal group (FIG. 14A). The treatment with autologous cardiomyocytes indicates that there was decreased need for endogenous angiogenesis and increased tissue perfusion as well as tissue repair within the infarct zone.

Figure 14B:
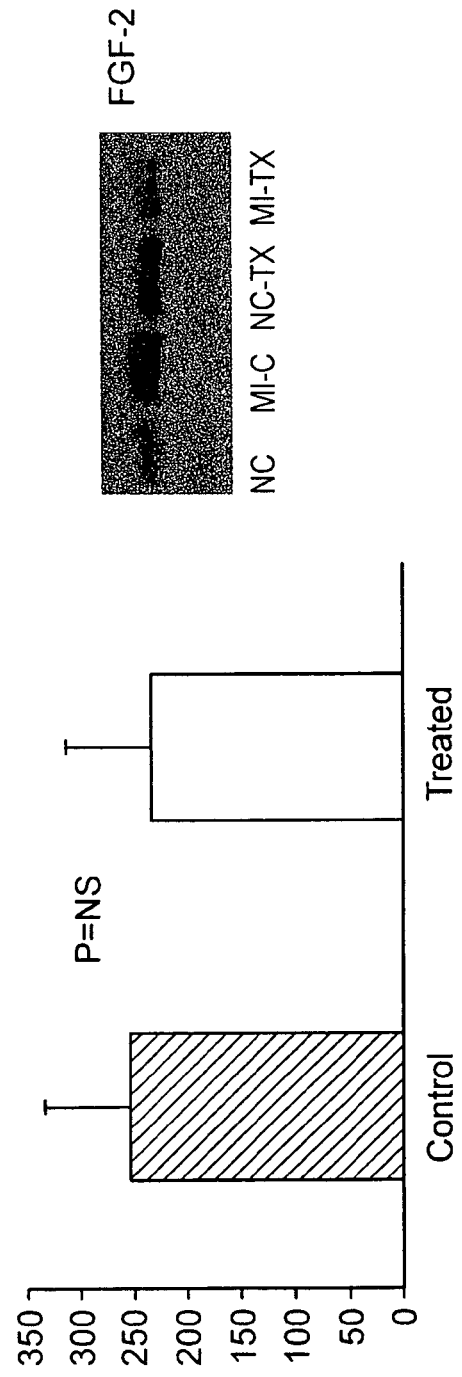

FGF-2 levels, on the other hand, tended to be equally elevated 3-4 fold above baseline in both groups (FIG. 14B).

Figure 15A:
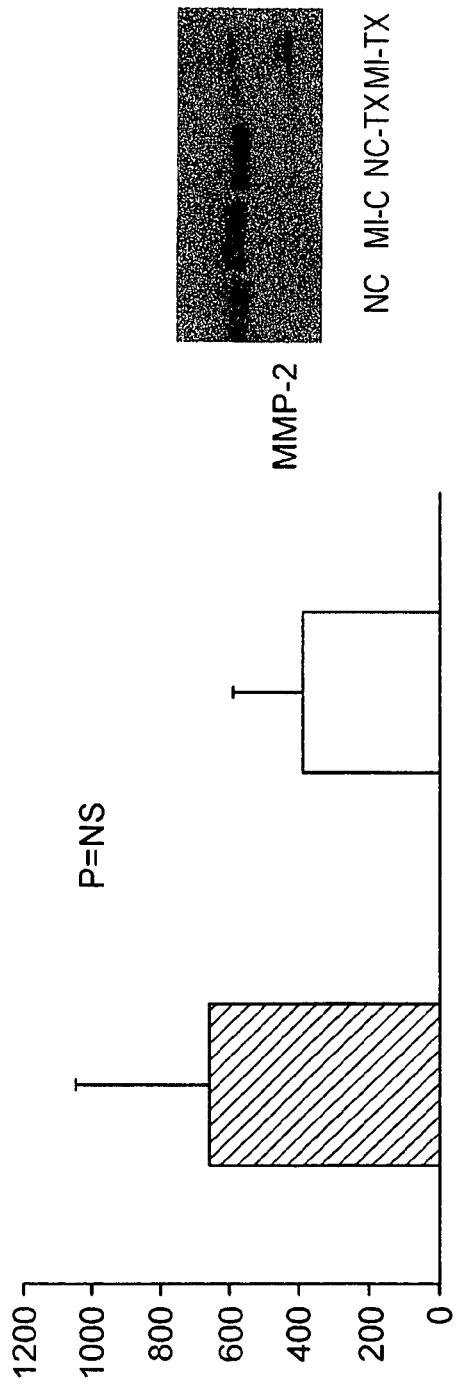
FIGS. 15A and 15B show the matrix metalloproteinase expression for MMP-2 and TIMP-2, respectively.
Figure 15B:
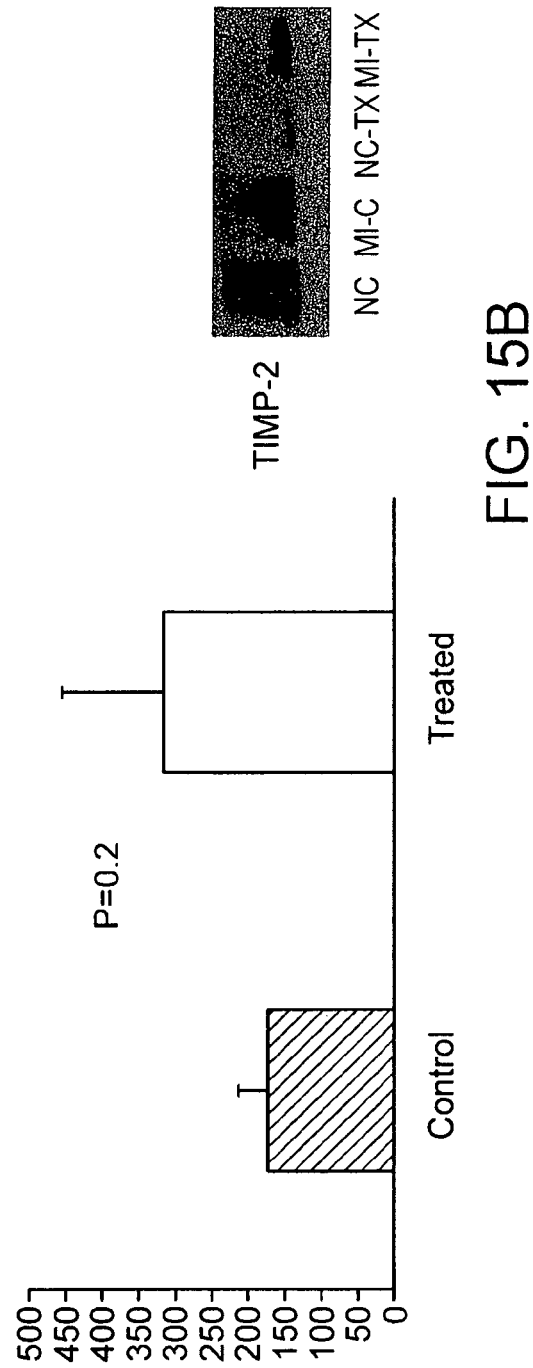

Given the observed effect of myotissue on preventing myocardial dysfunction and left ventricular dilation, the expression of matrix metalloproteinases MMP-2 and -9 was evaluated, as well as tissue inhibitor of matrix metalloproteinase-2 (TIMP-2) that are known to be involved in unfavorable remodeling post-infarction. Preserved myocardial function in treated animals correlated with a trend to two-fold lower levels of MMP-2 (FIG. 15A) and two-fold higher levels of TIMP-2 (FIG. 15B). MMP-9 levels were down-regulated in both animal groups as would be expected from the kinetics of MMP-9 post myocardial infarction.

The embodied methods, which obviate the need for cell culture with its potential complications of infection and decreased cell survival, can be implemented during planned revascularization procedure such as coronary artery bypass grafting (CABG), or via video assisted thoracoscopy for patients who are not candidates for revascularization. These results demonstrate that implantation of myotissue prevents inexorable decline in myocardial function observed after extensive anterior myocardial infarction. This was evident in preservation of ejection fraction, as well as hemodynamic parameters in the treated animals. This is in keeping with the results of prior results in which ejection fraction increased by about 3-7% in acute myocardial infarction setting.

Figure 16:
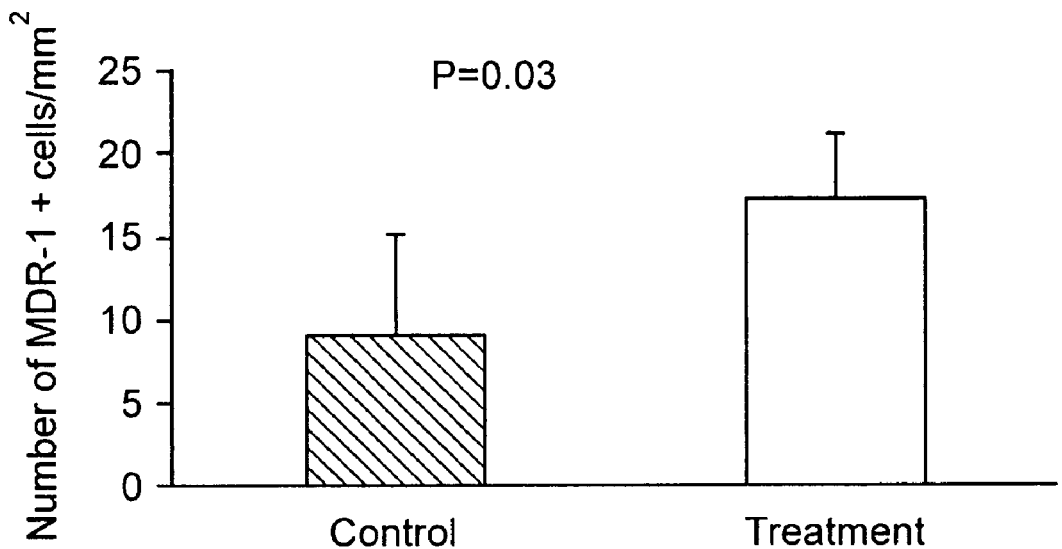
FIG. 16 shows the mdr-1 increase for treated animals.

Cardiomyoplasty in chronic ischemia was shown to decrease infarct size and contractility by SPECT and MRI imaging, respectively, in female mice post-myocardial infarction and were shown to form new vessels. This mechanism is at work given the overall increased number of mdr-1 positive stem cells in the infarct zone of treated animals surrounding the implant sites (FIG. 16). Mdr-1 positive cells have been shown to differentiate into myocytes, endothelial cells, smooth muscle cells and fibroblasts.

Sca-1 is expressed on endothelial cells in addition to stem cells. The present numbers of sca-1 positive cells were equivalent between the groups, possibly because of endothelial-staining confounding the true number of sca-1 positive stem cells.

Figure 17:
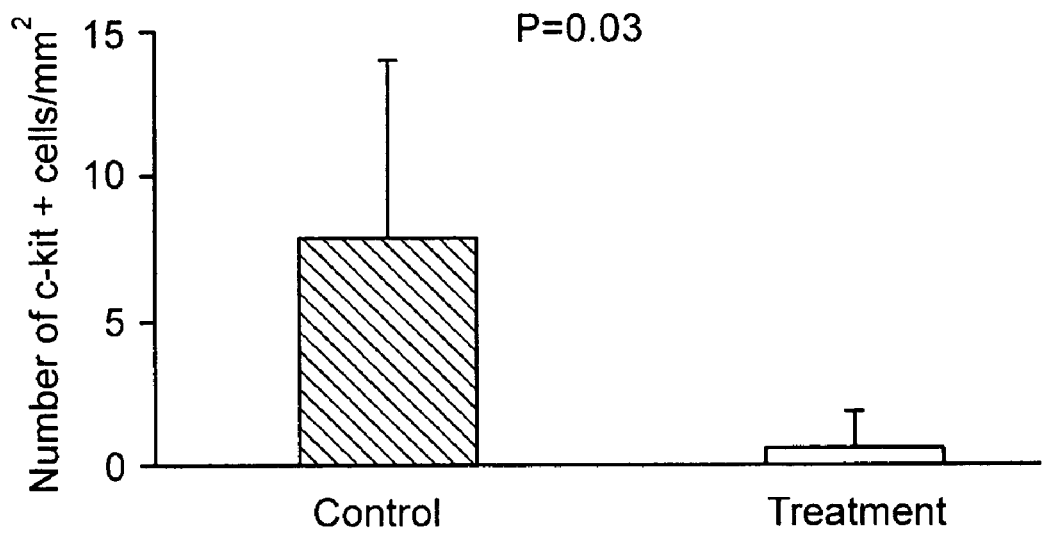
FIG. 17 shows the decrease in c-kit positive for treated animals.
Figure 18:
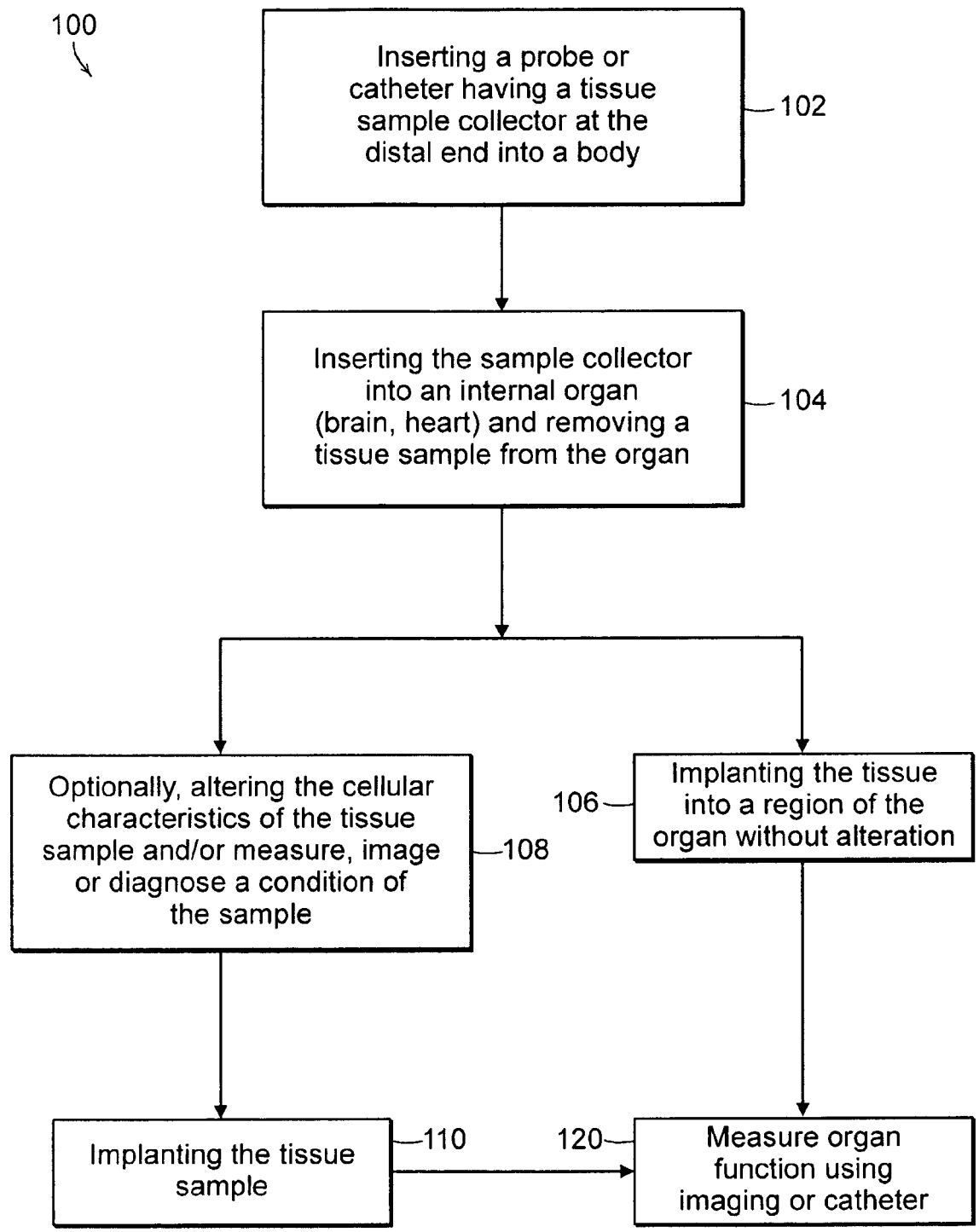
FIG. 18 illustrates a method for removal and implant of a portion of an organ in accordance with a preferred embodiment of the invention.

C-kit positive cells can regenerate multiple lineages and may be more pleuripotent than mdr-1 and sca-1 positive cells. An increase in c-kit positive cells was found in untreated samples (FIG. 17). Less mature c-kit positive stem cells are in this case derived from bone marrow and recruited in higher numbers to the infarct area given the absence of implant-derived mdr-1 and sca-1 cardiomyocyte progenitors.

In adult murine myocardium, sca-1 positive c-kit negative cells express cardiogenic transcription factors but not the structural genes making them candidates for cardiac progenitor cells. Indeed, sca-1 positive c-kit negative cells home to the infarct-border zone and make up as many as 15% of the myocyte population in this region.

In hypertrophied hearts the numbers of c-kit, mdr-1, and sca-1 positive cells are also increased compared to controls. The numbers of these cells are not equal, however, with c-kit cells outnumbering sca-1 and mdr-1 cells in this order, suggesting that cardiac progenitors may express these markers at different stages of differentiation. It is possible that mdr-1 positive cells are more differentiated than c-kit positive cells and, therefore, owing to the enriched environment of the implants, have a greater survival and differentiation rate in the treated animals.

There is an alternative explanation for this enrichment in mdr-1 positive cells in the treated animals. Rather than migrating directly from the implant into the infarct and peri-infarct zones, they may have been recruited from atria and right ventricular outflow tracts of the heart in response to the homing signals provided by the implant tissue.

Isl-1 cells, which are the post-natal cardioblasts, are most prevalent in these regions of the heart and may be recruited during myocardial infarction.

The differentiation potential of the adult cardiac stem cells is not only limited by their senescence, i.e., low expression of telomerase reverse transcriptase, but also likely by the trophic factor impoverished milieu of the infarct. In the past this problem was circumvented partly by implanting the myoblasts into peri-infarct hybernating zones using NOGA catheter electromechanical mapping guidance. However, by implanting stem cells together with adjacent intact differentiated cardiomyocytes, the stem cells with those trophic factors necessary for differentiation were provided.

Although stem cells are purportedly more durable than other cells, they also survive poorly in an infarcted and non-perfused environment. Thus, pro-angiogenic microenvironment created by the implants may have been another instrumental factor in increasing the number of viable mdr-1 positive cells.

Consistent with these measurements in acute myocardial infarction model, VEGF-2 levels were lower in treated animals at four (4) weeks after the initial myocardial infarction and two weeks after cardiomyoplasty treatment. Note that at four (4) weeks, post-myocardial infarction, when the ejection fraction and other parameters of myocardial function had recovered in animals treated with cardiomyoplasty, VEGF-2 levels can already down-regulated. Animals that were not treated and continue to have lower myocardial perfusion and myocardial dysfunction, still maintain elevated VEGF-2 levels.

In another embodiment of a method 100 in accordance with the invention, a sample can be taken from an animal or human brain and implanted into damaged or diseased tissue to provide cellular regeneration. The probe or catheter is first inserted 102 into the body, a sample collector is inserted 104 into the organ and a tissue sample is removed. The collector can either be repositioned for implantation 106 without any alteration of the sample, or alternatively, the sample can be measured 108 or its cellular characteristics altered prior to implantation 110. The organ function can then be evaluated 120 or monitored.

While the invention is described through the above-described exemplary embodiments, it will be understood by those of ordinary skill in the art that modifications to, and variations of, the illustrated embodiments may be made without departing from the inventive concepts disclosed herein. Accordingly, the invention should not be viewed as limited, except by the scope and spirit of the appended claims.

What is claimed is:

1. A method of transplanting tissue from a septal region of a mammalian myocardium to a second region of the mammalian myocardium, the method comprising:
    removing a tissue sample from the septal region of the mammalian myocardium, the tissue sample including a tissue scaffold; and
    implanting the tissue sample with the tissue scaffold in the second region of the mammalian myocardium to increase cellular growth in the second region.

2. The method of claim 1, further comprising removing the tissue sample from intact myocardial tissue, the tissue scaffold including extracellular supporting tissue structure.

3. The method of claim 2 further comprising removing the tissue sample from a ventricle septum of the myocardium using a catheter.

4. The method of claim 1 further comprising implanting the tissue sample into ischemic myocardial tissue.

5. The method of claim 1 further comprising implanting the tissue sample without cellular alteration.

6. The method of claim 1 further comprising inserting a tube into the septal region of mammalian myocardium to cut the tissue sample from the first region.

7. The method of claim 6 further comprising inserting the tube into the septal region, the tube having a diameter between 200 microns and 800 microns.

8. The method of claim 6 further comprising inserting a catheter into a mammalian body, the catheter having the tube on a distal end of the catheter.

9. The method of claim 6 further comprising inserting the tube into the septum, the tube having a length that extends through the septum.

10. The method of claim 6 further comprising moving a stylet within the tube to insert the tissue sample into the second region.

11. The method of claim 1 further comprising inserting a cannula into the septal region of tissue to remove the tissue sample.

12. A method of treating a mammalian subject having injured myocardial tissue, the method comprising:
    removing a tissue sample from a septal region of mammalian myocardial tissue of the mammalian subject with a catheter, the tissue sample including a tissue scaffold; and
    implanting the tissue sample with the tissue scaffold in a second region of injured mammalian myocardial tissue of the mammalian subject to enhance cellular growth.

13. The method of claim 12 further comprising performing a plurality of removing and implanting steps with a plurality of tissue samples.

14. The method of claim 12 further comprising performing the method after myocardial infarction by implanting to the tissue sample in an infarcted tissue region.

15. The method of claim 12 further comprising inserting a distal end of the catheter into a subject, positioning the distal end of the catheter adjacent to tissue to be removed, inserting a tubular device at the distal end of the catheter into the tissue, removing a tissue sample from the septal region of tissue with the tubular device, repositioning the catheter such that the tubular device is adjacent on implant region, inserting the tubular device into the implant region to implant the tissue sample.

16. The method of claim 12 further comprising implanting the tissue sample without cellular alteration.

17. The method of claim 12 further comprising inserting a probe with a tube having a diameter between 200 microns and 800 microns into the tissue.

18. The method of claim 17 further comprising inserting a tube having a sharp distal edge.

19. The method of claim 12 further comprising inserting a tube through a ventricular septum to remove the tissue sample.

20. A method of improving cardiac function in a mammalian subject having an injured myocardium, the method comprising:
    removing a tissue sample from a septal region of a mammalian myocardium of the mammalian subject, the tissue sample including a tissue scaffold;
    performing a diagnostic or therapeutic method with the tissue sample; and
    implanting the tissue sample with the tissue scaffold in a second region of the mammalian myocardium of the subject.

21. The method of claim 20 further comprising wherein the performing step further comprises inserting an angiogenic protein into the tissue sample.

22. The method of claim 20 wherein the performing step further comprises inserting cellular material into the tissue sample.

23. The method of claim 20 further comprising inserting a tube into a septum to remove the tissue sample.

24. The method of claim 20 further comprising implanting the tissue sample into an infarcted region of tissue.

25. A method of transplanting tissue from a septal region of a mammalian myocardium to a second region of the mammalian myocardium, the method comprising:
    removing a tissue sample from the septal region of the mammalian myocardium, the tissue sample including a tissue scaffold;
    altering a cellular characteristic within the tissue scaffold of the tissue sample; and
    implanting the tissue sample with the tissue scaffold in the second region of the mammalian myocardium to increase cellular growth in the second region.

26. The method of claim 25, wherein the step of altering the cellular characteristic comprises removing a cellular component from the tissue scaffold and inserting a material into the tissue scaffold.

27. The method of claim 25 further comprising inserting an angiogenic protein into the tissue scaffold.

28. The method of claim 25 further comprising forming a cellular material and inserting the cellular material into the tissue scaffold.

29. The method of claim 25 further comprising inserting transfected cardiomyocytes or endothelial progenitors into the tissue scaffold.

30. A method of transplanting tissue from a septal region of a mammalian myocardium to a second region of the mammalian myocardium, the method comprising:
    inserting a catheter into a mammalian body;
    inserting a distal end of the catheter through the septal region to separate a tissue sample from the septal region;
    removing the tissue sample from the septal region of the mammalian myocardium with the catheter, the tissue sample including a tissue scaffold; and
    implanting the tissue sample with the tissue scaffold in the second region of the mammalian myocardium with the catheter to increase cellular growth in the second region.

31. The method of claim 30, further comprising removing the tissue sample from intact myocardial tissue of a patient by moving a stylet at the distal end of catheter with a cable extending through the catheter to a proximal end.

32. The method of claim 30 further comprising removing the tissue sample from a ventricle septum of the myocardium with a tube on a distal end of the catheter, the tube having a sharp distal end and a movable stylet.

33. The method of claim 30 further comprising implanting the tissue sample into ischemic myocardial tissue.

34. The method of claim 30 further comprising implanting the tissue sample without cellular alteration.

35. The method of claim 30 further comprising performing a plurality of removing and implanting steps with a plurality of tissue samples.

36. The method of claim 30 further comprising performing the method after myocardial infarction by implanting the tissue sample in an infarcted tissue region.

37. The method of claim 30 further comprising inserting a distal end of a catheter into the patient, positioning the distal end adjacent to septal tissue to be removed, inserting a tubular device into the septal tissue, removing a tissue sample from the septal tissue, repositioning the catheter such that the tubular device is adjacent on implant region, inserting the tubular device into the implant region to implant the tissue sample.

38. The method of claim 30 further comprising inserting the catheter through an endoscope.

39. The method of claim 30 further comprising using a guide catheter to insert a tube to cut tissue from the septal region.

40. The method of claim 30 further comprising viewing the removal of the tissue sample with an endoscope.

* * * * *